United States Patent [19]

Pomogailo et al.

[11] 4,147,664
[45] Apr. 3, 1979

[54] CATALYST OF POLYMERIZATION, COPOLYMERIZATION AND OLIGOMERIZATION OF OLEFINS AND DROLEFINS

[76] Inventors: Anatoly D. Pomogailo, ulitsa Pervaya, 21; Alla P. Lisitskaya, ulitsa Pervaya, 2, kv. 27; Viktor S. Oskin, ulitsa Pervaya, 1, kv. 6; Fridrikh S. Dyachkovsky, ulitsa Tretya, 2, kv. 2; Ardalion N. Ponomarev, ulitsa Tretya, 2, kv. 3; Nina S. Gorkova, ulitsa Pervaya, 24, kv. 19, all of Moskovskaya oblast, Noginsky raion, Chernogolovka, U.S.S.R.

[21] Appl. No.: 796,480

[22] Filed: May 12, 1977

Related U.S. Application Data

[63] Continuation of Ser. No. 625,516, Oct. 24, 1975, abandoned.

[51] Int. Cl.$^2$ .............................................. C08F 4/02
[52] U.S. Cl. ........................... 252/429 B; 252/429 C; 252/431 R; 252/431 C; 252/431 N; 260/683.15 B; 260/683.15 D; 526/140; 526/141; 526/142
[58] Field of Search ........... 252/429 B, 429 C, 431 R, 252/431 C, 431 N

[56] References Cited

U.S. PATENT DOCUMENTS

| | | | |
|---|---|---|---|
| 3,152,088 | 10/1964 | Sandri et al. | 252/429 B |
| 3,396,155 | 8/1968 | Delbouille et al. | 252/431 R X |
| 3,594,330 | 7/1971 | Delbouille et al. | 252/429 C |
| 3,737,474 | 6/1973 | Dunn | 252/429 B X |

*Primary Examiner*—Patrick Garvin
*Attorney, Agent, or Firm*—Haseltine, Lake & Waters

[57] ABSTRACT

A catalyst for polymerization, copolymerization and oligomerization of olefins and diolefins is described, which is a compound having the general formula $MX_n$ wherein M is a metal belonging to IVA — VIA groups of the Periodic System or a cobalt, X is a halogen, hydrogen, cyclopentadienyl, alkoxy-, aryloxy-, or amido group, and n is an integer denoting the valency of M; a compound having the general formula $M'R_pZ_{k-p}$ wherein M' is a metal of I—III groups of the Periodic System, R is a hydrocarbon radical, Z is a halogen, hydrogen, alkoxy-, aryloxy- or amido group, k is an integer denoting the valency of M', $1 \leq p \leq k$; or compound having the general formula $MR_mX_{n-m}$, wherein $2 \leq m \leq n$, said component being chemically bonded with the surface of a carbon-chain polymer carrier through the fragment

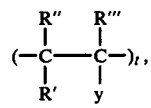

wherein
R' = H, CH$_3$, C$_2$H$_5$, CH$_2$ = CH$_2$, C$_6$H$_5$;
R'' = H, or CH$_3$;
R''' = H, or CH$_3$;
y = OH, NHR', SR; COCH$_3$, CH$_2$OH

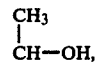

CH$_2$NHR', COOH, OCOCH$_3$, CH$_2$SH, COOCH$_3$, C≡N, N(R')$_2$, SO$_2$R', SOR', —CH$_2$—S—CH$_2$—CH=CH$_2$, —CH$_2$—NH—CH$_2$—CH=CH$_2$, —CH$_2$—SO$_2$—CH$_2$—CH=CH$_2$,

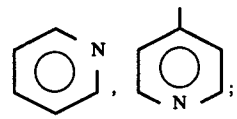

wherein R' is defined above,
t is the degree of polymerization equal to 4 - 5000.

In the case where use is made of compound $MX_n$ applied to a carbon-chain polymer carrier, it is activated with compound $M'R_pZ_{k-p}$, while in the case of use being made of compound $M'R_pZ_{k-p}$ applied to a carbon-chain polymer carrier, it is activated with compound $MX_n$.

Said catalyst is several times (5 to 100) more active than prior art catalysts and provides for a high yield of the product, which may be as high as 1000 kg/g of a transition metal.

26 Claims, No Drawings

CATALYST OF POLYMERIZATION, COPOLYMERIZATION AND OLIGOMERIZATION OF OLEFINS AND DROLEFINS

This invention relates to catalytic polymerization processes, and more particularly it relates to complex catalysts for polymerization, copolymerization, and oligomerization of olefins and diolefins. Said catalysts are widely used in the manufacture of polyethylene, polypropylene, and copolymers of ethylene with propylene and with butene, and also for producing ethylene-propylene-diolefin rubbers and oligomeric olefins according to the so-called low-pressure method (Ziegler process).

Known in the art are catalysts for polymerization, copolymerization, and oligomerization of olefins, which are binary systems consisting of components of a compound of a transition metal having the formula $MX_n$, where M is a metal or oxide of a metal belonging to IVA-VIA or VIII groups of the Periodic System, X is a halogen, hydrogen, alkoxy-, aryloxy-, amido-, or cyclopentadienyl group, and n is an integer denoting the valency of the metal M, and of a component of an organometallic compound having the general formula $M'R_pZ_{k-p}$, where M' is a metal of I-III groups of the Periodic System, R is a hydrocarbon radical, Z is a halogen, alkoxy-, or amido- groups, k is an integer denoting the valency of the metal M', and $1 \leq p \leq k$ (see, for example, Norman G. Gaylord, Hermal F. Mark. Linear and stereoregular addition polymers: polymerization with controlled propagation. 1959. Interscience Publishers, Inc., New York).

In order to increase the activity of said complex catalysts for polymerization and copolymerization of olefins, and also in order to control the kinetic parameters of the polymerization process induced by them, and the properties of the polymers formed, separate components of the catalyst, or the products of their interaction are fixed on a carrier of an inorganic type, this carrier being oxides, hydroxides, or oxyhalogenides of certain metals.

Indeed, the activity of such catalysts increases, but the inorganic carrier remains in the obtained polymer and this increases its ash content. In recent years attempts were made to eliminate this disadvantage. To this end, catalysts were offered, these being catalysts for polymerization, and copolymerization of olefins and diolefins on polymer carriers; carbon and hetero-chain polymers, containing fragments capable of fixing said compounds, $MX_n$ or $M'R_pZ_{k-p}$. For example a catalyst is known, which is a product of interaction of the $TiCl_4$ and hydroxyl groups of crushed cellulose, polyatomic alcohols, polyglycols, activated with diethyl-aluminium chloride (British Pat. No. 834,217, CII(1)BOIj, May 4, 1960). Known also is a catalyst for polymerization and copolymerization of olefins, consisting of a product of interaction of $TiCl_4$ with hydrolyzed copolymer of ethylene and vinylacetate, or with vinyl chloride, containing from 1 to 20 percent of hydroxyl groups, activated with an organoaluminium compound. $TiCl_4$ is fixed on such polymers due to their hydroxyl groups when the component solutions are mixed together, the chemistry being as follows:

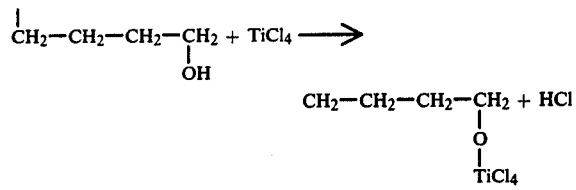

(French Pat. Nos. 1,405,372 and 1,588,369).

Known also are catalysts for polymerization and copolymerization of olefins containing the product of reaction of $MX_n$ with nitrogen-containing polymers, having in their compositions the functional amino-, imino-, imido-, urethane-, nitrile, or nitro-group (Belgian Pat. No. 706,659, Class CO8f, May 17, 1968), and also with sulphur-containing polymers, for example, polysulphone (Belgian Pat. No. 690,008 Cl.CO8f, May 22, 1968), activated with organoaluminium compounds. Moreover, such catalysts are the products of interaction of $MX_n$ with carbon-chain polymers having fragments containing elements with unshared pairs of electrons ($>\dot{N}-$, $-\dot{O}-$, $-\dot{S}-$, or $>\dot{P}-$ Inventor's Certificate of the USSR, No. 420,330, Cl.BOIj, 11/84, 1974), activated with organoaluminium compounds.

Finally, catalysts of polymerization and copolymerization are known consisting of a mixture of $MX_n$ and organoaluminium compound fixed on a polymer carrier, containing groups $>C=O$, $>C=N-$, or $C=N$ (Belgian Pat. No. 716,375, cl. CO8f, Dec. 11, 1968).

However, the above-named catalysts for polymerization and copolymerization do not meet the requirements of modern industry producing polyolefins, insofar as they have a number of disadvantages that considerably limit, and in some cases exclude the possibility of using them. Most essential disadvantages inherent in the known catalysts of polymerization and copolymerization of olefins are listed below.

1. Relatively low activity in reactions of polymerization and copolymerization of olefins and diolefins (for example, the yield of polyethylene does not exceed 1-2 kg/g M), due to the fact that a significant part of the component ($MX_n$ or $M'R_pZ_{k-p}$) fixed on a polymer carrier is confined in the volume of the polymer carrier and does not take part in the formation of active centres of polymerization. The degree of utilization of the applied components is not greater than 2-3 percent.

2. The necessity of a complex operation for washing off the residues of the catalyst (after its use in the polymerization process) which decrease the stability of the obtained products.

3. The consumption coefficients, with respect to the second component of the catalyst ($M'R_pZ_{k-p}$), are high when $MX_n$ is fixed on the polymer carrier. This involves an unreasonable consumption of the catalyst in the reaction with vacant fragments that are always present in such polymer carriers.

4. The polymer carrier of the catalyst produces an unfavourable effect on the properties of the obtained polyolefins or their copolymers since it is not always sufficiently compatible with the obtained products owing to the different nature thereof.

5. The above-named polymer carriers obtained by the polymerization or copolymerization with expensive monomers are not easily available.

6. The properties of the obtained products of polymerization (molecular weight, bulk weight, and composition) are difficult to control.

It is an object of this invention is to provide a catalyst for polymerization and copolymerization of olefins and diolefins that would ensure higher yields of polymer compared with the known catalysts.

Another object of the invention is to provide a catalyst for polymerization and copolymerization of olefins and diolefins that would provide conditions for easy control of the bulk and molecular weight of the products formed in the polymerization process.

Still another object of the invention is to provide a catalyst for polymerization and copolymerization of olefins and diolefins that would eliminate the necessity of washing off the residual catalyst from the obtained polymers and thus simplify the process flowsheet.

Moreover, the object of this invention is to provide a catalyst for polymerization and copolymerization of olefins and diolefins having such properties that would widen the limits of its uses.

Yet another object of the invention is to provide a catalyst for polymerization and copolymerization of olefins and diolefins that would incorporate a polymer carrier which is an industrial product on the one hand, and, with respect to its properties, would be identical or close to the obtained polymers on the other hand.

Said objects have been accomplished by the provision of a catalyst for polymerization and copolymerization of olefins and diolefins, which, according to the invention, is one of the following components: component A, which is actually a compound having the formula $MX_n$, where M is a metal belonging to IVA-VIA groups of the Periodic System or cobalt, X is a halogen, hydrogen, cyclopendadienyl, alkoxyl, aryloxyl, or amido group, and n is an integer denoting the valency of the metal M; component B, which is an organometallic compound having the formula $M'R_pZ_{k-p}$, where M' is a metal of I-III groups of the Periodic System, R is a hydrocarbon radical, Z is a halogen, hydrogen, alkoxy-, aryloxy-, or amido group, k is an integer denoting the valency of the metal M', and $1=p=k$; component C, which is a product of interaction of the above-named $MX_n$ and $M'R_pZ_{k-p}$ having the formula $MR_mX_{n-m}$ where m is an integer and $2 \leq m \leq n$; each of the above-components being bonded chemically through one of the fragments having the formula

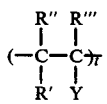

where
R′=H, CH₃, C₂H₅, CH=CH₂; C₆H₅,
R″=H, or CH₃;
R‴=H, or CH₃;
Y=OH, NHR′, SR′, COCH₃,

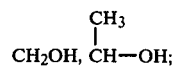

CH₂NHR′, CH₂SH, COOH, OCOCH₃, COOCH₃, C≡N, N(R′)₂, ≦SOR′

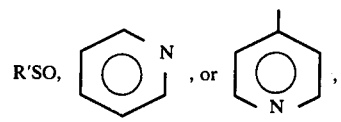

wherein R′ is as defined above,
t is the mean degree of polymerization equal from 4 to 5000, only with the surface of a carbon-chain polymer carrier, the component A being activated with the compound $M'R_pZ_{k-p}$, and the component B being activated with the compound $MX_n$.

The interaction between the compounds $MX_n$, $M'R_pZ_{k-p}$ and $MR_mX_{n-m}$ with carbon-chain polymers containing the above-named fragments on their surface was not known in the prior art.

According to the invention, the following modifications of a catalyst for polymerization and copolymerization of olefins and diolefins are proposed.

1. A catalyst in which component A is a compound having said formula $MX_n$, which is bonded chemically through a fragment

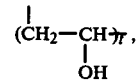

wherein t=5—1500, with the surface of the polymer carrier activated with one of the above-named organometallic compounds having the formula $M'R_pZ_{k-p}$.

The catalyst of this modification can be represented in the following manner:

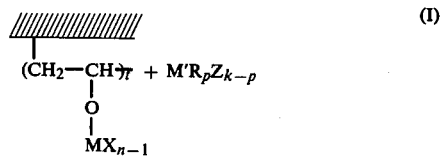
(I)

where ///////// shows schematically the surface of a carbon-chain polymer.

Some representatives of such catalysts are:
1. TiCl₄, chemically bonded with the surface of hydrolyzed polyethylene-gr.*-polyvinylacetate activated with Al(C₂H₅)₃Cl.

*Here and further in the text the abbreviation "gr." stands for "grafted".
2. TiCl₄, chemically bonded with the surface of hydrolyzed polyethylene-gr.-polyvinylacetate, activated with Al(C₂H₅)₃.

3. VCl₄, bonded chemically with the surface of hydrolyzed polypropylene-gr.-polyvinylacetate, activated with Al(C₂H₅)₂Cl.

4. VCl₄, bonded chemically with the surface of hydrolyzed polystyrene-gr.-polyvinylacetate, activated with Al(iso—C₄H₉)₂H.

5. VCl₄, bonded chemically with the surface of hydrolyzed poly(ethylene-co-propylene)-gr.-polyvinylacetate, activated with Al(C₂H₅)₂Cl.

6. MoCl₅, bonded chemically with the surface of hydrolyzed polyethylene-gr.-polyvinylacetate, activated with Al(C₂H₅)₂Cl.

7. Ti(O-C₄H₉)₄, bonded chemically with the surface of hydrolyzed polyethylene-gr.-polyvinylacetate, activated with Al(C₂H₅)₂Cl.

8. $(C_2H_5)_2TiCl_2$, bonded chemically with the surface of hydrolyzed polyethylene-gr.-polyvinylacetate, activated with $Al(C_2H_5)_2Cl$.

9. $(C_2H_5)_2TiCl_2$, bonded chemically with the surface of hydrolyzed polyethylene-gr.-polyvinylacetate, activated with $Al(iso-C_4H_9)_2Cl$.

II. A catalyst in which component A is a compound having said formula $MX_n$ bonded chemically through the fragment

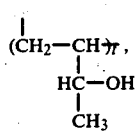

where $t=100-2000$ with the surface of a polymer carrier activated with an organometallic compound having said formula $M'R_pZ_{k-p}$. The catalyst of this type can be described as follows:

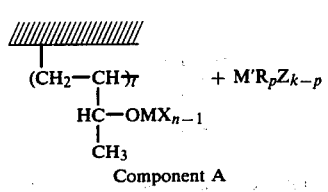

Component A

Some representatives of this catalyst are:

1. $TiCl_4$, bonded chemically with the surface of reduced polyethylene-gr.-polymethylvinylketone, activated with $Al(C_2H_5)_2Cl$.

2. $VCl_4$, bonded chemically with the surface of reduced polyethylene-gr.-polymethylvinylketone, activated with $Al(C_2H_5)_2Cl$.

3. $Ti(O-C_2H_5)_2$, bonded chemically with the surface of reduced polyethylene-gr.-polymethylvinylketone activated with $Al(C_2H_5)_2Cl$.

4. $(C_5H_5)_2TiCl_2$, bonded chemically with the surface of reduced polyethylene-gr.-polymethylvinylketone, activated with $Al(C_2H_5)_2Cl$.

5. $MoCl_5$, bonded chemically with the surface of reduced polyethylene-gr.-polymethylvinylketone, activated with $Al(C_2H_5)_2Cl$.

6. $TiCl_4$, bonded chemically with the surface of reduced poly(ethylene-co-propylene)-gr.-polymethylvinylketone, activated with $Al(C_2H_5)_2Cl$.

7. $VOCl_3$, bonded chemically with the surface of reduced polystyrene-gr.-polymethylvinylketone, activated with $Al(iso-C_4H_9)_2Cl$.

III. A catalyst in which component A is one of the compounds having the formula $MX_n$, bonded chemically through the fragment

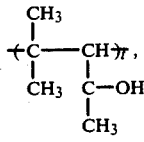

where $t=30-300$ with the surface of a polymer carrier activated with one of the organometallic compounds having the formula $M'R_pZ_{k-p}$.

The catalyst of this type can be represented as follows:

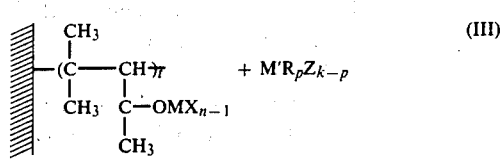

Some representatives of this catalyst are: 1. $TiCl_4$, bonded chemically with the surface of reduced polyethylene-gr.-polyisopropylideneacetone, activated with $Al(C_2H_5)_2Cl$.

2. $VCl_4$, bonded chemically with the surface of reduced polyethylene-gr.-isopropylideneacetone, activated with $Al(iso-C_4H_9)_2Cl$.

3. $VOCl_3$, bonded chemically with the surface of reduced polystyrene-gr.-polyisopropylideneacetone, activated with $Al(C_2H_5)_2Cl$.

IV. A catalyst in which component A is one of the compounds having the formula $MX_n$, bonded chemically through the fragment

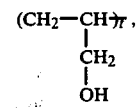

where $t=4-9$ with the surface of a polymer carrier activated with one of the organometallic compounds having the formula $M'R_pZ_{k-p}$.

The catalyst of this type can be shown schematically as follows:

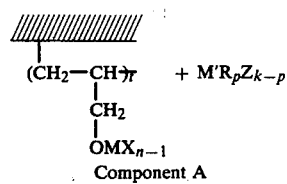

Component A

Some representatives of this catalyst are as follows:
1. $TiCl_4$, bonded chemically with the surface of polyethylene-gr.-polyallyl alcohol activated with $Al(C_2H_5)_2Cl$.

2. $TiCl_4$, bonded chemically with the surface of the polypropylene-gr.-polyally alcohol, activated with $Al(iso-C_4H_9)_2H$.

3. $VCl_4$, bonded chemically with the surface of poly(ethylene-co-propylene)-gr.-polyallyl alcohol, activated with $Al(iso-C_4H_9)_2Cl$.

4. $VOCl_3$, bonded chemically with the surface of polystyrene-gr.-polyallyl alcohol, activatd with $Al(C_2H_5)_3$. 5. $VCl_4$, bonded chemically with the surface of polyethylene-gr.-polyallyl alcohol activated with $Al(C_2H_5)_2Cl$.

6. $MoCl_5$, bonded chemically with the surface of polyethylene-gr.-polyallyl alcohol activated with $Al(C_2H_5)_2Cl$.

7. $WCl_6$, bonded chemically with the surface of polyethylene-gr.-polyallyl alcohol activated with $Al(C_2H_5)_2Cl$.

8. $Ti(OC_4H_9)_4$, bonded chemically with the surface of polyethylene-gr.-polyallyl alcohol activated with $Al(C_2H_5)_2Cl$.

9. $Ti(OC_4H_9)_4$, bonded chemically with the surface of polyethylene-gr.-polyallyl alcohol activated with $Al_2(C_2H_5)_3Cl_3$.

10. (C$_5$H$_5$)$_2$TiCl$_2$, bonded chemically with the surface of polyethylene-gr.-polyallyl alcohol activated with Al(C$_2$H$_5$)$_2$Cl.

11. VCl$_4$, bonded chemically with the surface of polyethylene-gr.-polyallyl alcohol activated with Zn(CH$_3$)$_3$.

12. VCl$_4$, bonded chemically with the surface of polyethylene-gr.-polyallyl alcohol activated with LiC$_4$H$_9$.

13. Ti(OC$_4$H$_9$)$_4$, bonded chemically with the surface of polyethylene-gr.-polyallyl alcohol activated with AlC$_2$H$_5$Cl$_2$.

V. A catalyst in which component A is one of the compounds having the formula MX$_n$, bonded chemically through the fragment

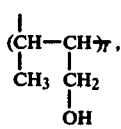

where t=4—9 with the surface of a polymer carrier activated with one of the organometallic compounds having the formula M'R$_p$Z$_{k-p}$.

The catalyst of this type can be described schematically as follows:

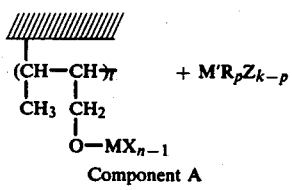

Component A

Some representatives of this catalyst are:

1. TiCl$_4$, bonded chemically with the surface of polyethylene-gr.-polycrotyl alcohol activated with Al(C$_2$H$_5$)$_2$Cl.

2. VCl$_4$, bonded chemically with the surface of polystyrene-gr.-polycrotyl alcohol activated with Al(iso-C$_4$H$_9$)$_2$Cl.

3. VCl$_4$, bonded chemically with the surface of polyethylene-gr.-polycrotyl alcohol activated with Al(iso-C$_4$H$_9$)$_2$H.

VI. A catalyst in which component A is one of the compounds having the formula MX$_n$, bonded chemically through the fragment

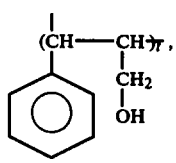

where t=4—9 with the surface of a polymer carrier activated with an organometallic compound having the formula M'R$_p$Z$_{k-p}$.

The catalyst of this type can be shown schematically as follows:

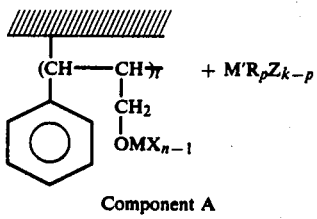

Component A

Some representatives of this catalyst are:

1. TiCl$_4$, bonded chemically with the surface of polyethylene-gr.-polycinnamic alcohol activted with Al(C$_2$H$_5$)$_2$Cl.

2. VCl$_4$, bonded chemically with the surface of polyethylene-gr.-polycinnamic alcohol activated with Al(C$_2$H$_5$)$_2$Cl.

VII. A catalyst in which component A is a compound having the formula MX$_n$, bonded chemically through the fragment

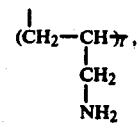

where t=500—2000 with the surface of a polymer carrier activated with an organometallic compound having the formula M'R$_p$Z$_{k-p}$.

The catalyst of this type can be described schematically as follows:

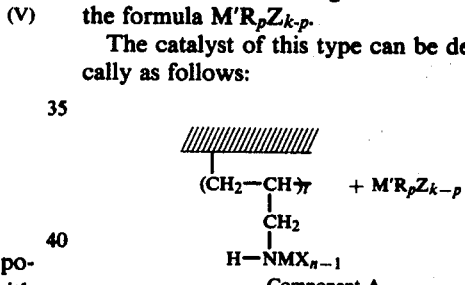

Component A

Some representatives of this catalyst are:

1. TiCl$_4$, bonded chemically with the surface of reduced polyethylene-gr.-polyacrylonitrile activated with Al(C$_2$H$_5$)$_2$Cl.

2. VCl$_4$, bonded chemically with the surface of reduced polyethylene-gr.-polyacrylonitrile activated with Al(C$_2$H$_5$)$_2$Cl.

VOCl$_3$, bonded chemically with the surface of reduced polyethylene-gr.-polyacrylonitrile activated with Al(C$_2$H$_5$)$_2$Cl.

VIII A catalyst in which component A is a compound having the formula MX$_n$, bonded chemically through the fragment

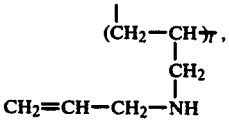

where t=4—9 with the surface of a polymer carrier activated with an organometallic compound having the formula M'R$_p$Z$_{k-p}$.

The catalyst of this type can be represented as

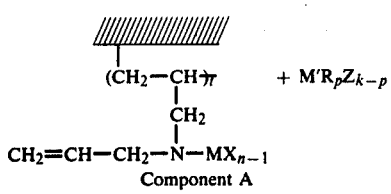

(VIII)

Component A

Some of the representative of this catalyst are as this:
1. TiCl$_4$, bonded chemically with the surface of polyethylene-gr.-polydiallylamine activated with Al(C$_2$H$_5$)$_2$Cl.
2. VCl$_4$, bonded chemically with the surface of polyethylene-gr.-polydiallylamine, activated with Al(C$_2$H$_5$)$_2$Cl.
3. VOCl$_3$, bonded chemically with the surface of polypropylene-gr.-polydiallylamine activated with AL(C$_2$H$_5$)$_2$Cl.
4. MoCl$_5$, bonded chemically with the surface of poly(ethylene-co-propylene)-gr.-polydiallylamine activated with Al(C$_2$H$_5$)$_2$Cl.
5. Ti(OC$_4$H$_9$)$_4$, bonded chemically with the surface of polyethylene-gr.-polydiallylamine activated with Al(C$_2$H$_5$)$_2$Cl.
6. (C$_5$H$_5$)$_2$TiCl$_2$, bonded chemically with the surface of polyethylene-gr.-polydiallylamine, activated with (C$_2$H$_5$)$_2$AlCl.
7. VCl$_4$, bonded chemically with the surface of polyethylene-gr.-polydiallylamine, activated with Al(iso-C$_4$H$_9$)$_2$H.
8. VO(OC$_2$H$_5$)$_3$, bonded chemically with the surface of polyethylene-gr.-polydiallylamine, activated with Al(C$_2$H$_5$)$_2$Cl.
9. VCl$_4$, bonded chemically with the surface of polystyrene-gr.-polydiallylamine, activated with Al(C$_2$H$_5$)$_2$Cl.

IX. A catalyst in which component A is a compound having the general formula MX$_n$, bonded chemically through the fragment

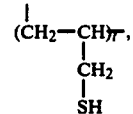

where t=4—9 with the surface of a polymer carrier activated with an organometallic compound having the formula M'R$_p$Z$_{k-p}$.

The catalyst can be described schematically as this:

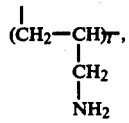

(IX)

Component A

Some representatives of this catalyst are:
1. TiCl$_4$, bonded chemically with the surface of polyethylene-gr.-polyallylamine, activated with Al(C$_2$H$_5$)$_2$Cl.
2. VCl$_4$, bonded chemically with the surface of polyethylene-gr.-polyallylamine, activated with Al(C$_2$H$_5$)$_2$Cl.
3. VOCl$_3$, bonded chemically with the surface of polystyrene-gr.-polyallylamine, activated with Al(iso-C$_4$H$_9$)$_2$Cl.

X. A catalyst in which component A is a compound having the general formula MX$_n$, bonded chemically through the fragment

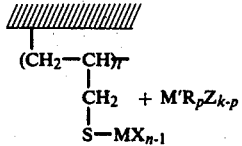

where t=4—9, with the surface of a polymer carrier activated with an organometallic compound having the formula M'R$_p$Z$_{k-p}$.

The catalyst of this type can be described as this:

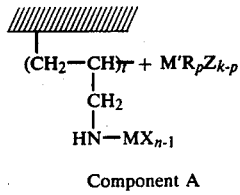

(X)

Some representatives of this catalyst are as follows:
1. TiCl$_4$, bonded chemically with the surface of polyethylene-gr.-polyallylmercaptan, activated with Al(C$_2$H$_5$)$_2$Cl.
2. VCl$_4$, bonded chemically with the surface of polyethylene-gr.-polyallylmercaptan, activated with Al(C$_2$H$_5$)$_2$Cl.
3. VCl$_4$, bonded chemically with the surface of polyethylene-gr.-polyallylmercaptan, activated with Al(iso-C$_4$H$_9$)$_2$H.
4. VCl$_4$, bonded chemically with the surface of poly(ethylene -co-propylene)-Polyallyl-mercaptan activated with Al(iso—C$_4$H$_9$)$_2$H.

XI. A catalyst in which component A is a compound having the formula MX$_n$m bonded chemically through the fragment

with the surface of a polymer carrier activated with an organometallic compound having the formula M'R$_p$Z$_{k-p}$.

The catalyst of this type can be described as follows

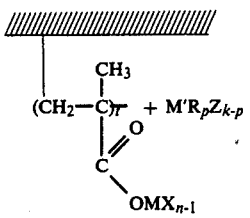

(XI)

Some representatives of the catalyst are as follows:
1. TiCl$_4$, bonded chemically with the surface of polyethylene-gr.-polymethacrylic activated with Al(C$_2$H$_5$)$_2$Cl.

2. VCl$_4$, bonded chemically with the surface of polypropylene-gr.-polymethacrylic acid, activated with Al(C$_2$H$_5$)$_2$Cl.

3. Ti(OC$_4$H$_9$)$_4$, bonded chemically with the surface of polyethylene-gr.-polymethacrylic acid, activated with Al(C$_2$H$_5$)$_2$Cl.

4. VCl$_4$, bonded chemically with the surface of polystyrene-gr.--polymethyacrylic acid, activated with Al(C$_2$H$_5$)$_2$Cl.

XII. A catalyst in which component A is a compound having the formula MX$_n$, bonded chemically through the fragment

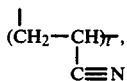

where t=500—2000 with the surface of a polymer carrier activated with an organometallic compound having the formula M'R$_p$Z$_{k-p}$.

The catalyst of this type can be represented as follows:

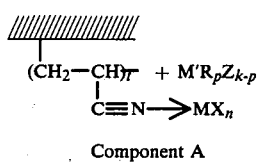

Component A

Some representatives of this catalyst are:

1. TiCl$_4$, bonded chemically with the surface of polyethylene-gr.-polyacrylonitrile activated with Al(C$_2$H$_5$)$_2$Cl.

2. VCl$_4$, bonded chemically with the surface of polyethylene-gr.-polyacrylonitrile, activated with Al(C$_2$H$_5$)$_3$.

3. VCl, bonded chemically with the surface of poly-(ethylene-co-propylene)gr.-polyacrylonitrile, activated with Al(C$_2$H$_5$)$_2$Cl.

4. VCl$_4$, bonded chemically with the surface of polypropylene-gr.-polyacrylonitrile, activated with Al(C$_2$H$_5$)$_2$Cl.

5. MoCl$_5$, bonded chemically with the surface of polyethylene-gr.-polyacrylonitrile, activated with Al(C$_2$H$_5$)$_2$Cl.

6. VCl$_4$, bonded chemically with the surface of polypropylene-gr.-polyacrylonitrile, activated with Al(iso-C$_4$H$_9$)$_2$H.

XIII. A catalyst in which component A is a compound having the general formula MX$_n$, bonded chemically through the fragment

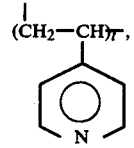

where $t$=500—5000 with the surface of a polymer carrier activated with an organometallic compound having the formula M'R$_p$Z$_{k-p}$.

The catalyst of this type can be described as follows:

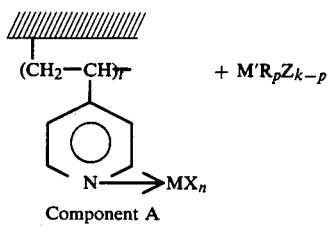

Some representatives of this catalyst are as follows:

1. TiCl$_4$, bonded chemically with the surface of polyethylene-gr.-poly(2-vinylpyridin), activated with Al(C$_2$H$_5$)$_2$Cl.

2. VCl$_4$, bonded chemically with the surface of polyethylene-gr.-poly(2-vinylpyridine) activated with Al(C$_2$H$_5$)$_2$Cl.

3. VCl$_4$ bonded chemically with the surface of polypropylene-gr.-poly(2-vinylpyridine) activated with Al(C$_2$H$_5$)$_3$.

4. VOCl$_3$, bonded chemically with the surface of polystyrene-gr.-poly(2-vinylpyridine) activated with Al(iso-C$_4$H$_9$)$_2$H.

XIV. A catalyst in which component A is a compound having the formula MX$_n$ bonded chemically through the fragment

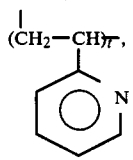

where t=500—5000 with the surface of a polymer carrier activated with an organometallic compound having the formula M'R$_p$Z$_{k-p}$.

The catalyst of this type can be described schematically as follows:

(XIV)

Component A

Some representatives of this catalyst are:

1. TiCl$_4$, bonded chemically with the surface of polyethylene-gr.-poly(4-vinylpyridine) activated with Al(C$_2$H$_5$)$_2$Cl.

2. VCl$_4$, bonded chemically with the surface of polyethylene-gr.-poly(4-vinylpyridine) activated with Al(C$_2$H$_5$)$_2$Cl.

3. VCl$_4$, bonded chemically with the surface of polypropylene-gr.-poly(4-vinylpyridine) activated with Al(C$_2$H$_5$)$_2$Cl.

4. VOCl$_3$, bonded chemically with the surface of polystyrene-gr.-poly(4-vinylpyridine) activated with Al(iso-C$_4$H$_9$)$_2$H.

5. CoCl$_2$, bonded chemically with the surface of polyethylene-gr.-poly(4-vinylpyridine) activated with Al(C$_2$H$_5$)$_2$Cl.

XV. A catalyst in which component A is a compound having the formula MX$_n$, bonded chemically through the fragment

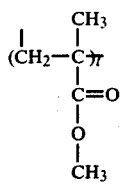

where t=400—4000 with the surface of a polymer carrier activated with an organometallic compound having the formula $M'R_pZ_{k-p}$.

The catalyst of this type can be described schematically as follows:

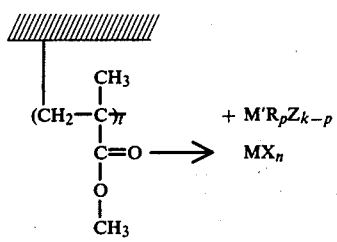

(XV)

Some representatives of this catalyst are:

1. $TiCl_4$, bonded chemically with the surface of polyethylene-gr.-polymethylmethacrylate actiavated with $Al(C_2H_5)_2Cl$.

2. $VOCl_3$, bonded chemically with the surface of polystyrene-gr.-polymethylmethacrylate, activated with $Al(C_2H_5)_2Cl$.

XVI. A catalyst in which component A is a compound having the formula $MX_n$ bonded chemically through the fragment

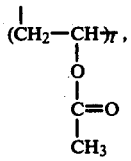

where t=50—1500 with the surface of a polymer carrier, activated with an organometallic compound having the formula $M'R_pZ_{k-p}$.

The catalyst of this type can be described schematically as follows:

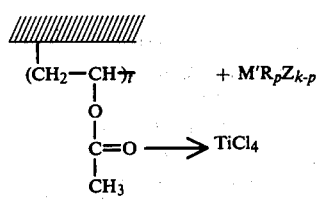

(XVI)

Some representatives of this catalyst are:

1. $TiCl_4$ bonded chemically with the surface of polyethylene-gr.-polyvinylacetate activated with $Al(C_2H_5)_2Cl$.

2. $TiCl_4$, bonded chemically with the surface of polystyrene-gr.-polyvinylacetate, activated with $Al(iso-C_4H_9)_2Cl$.

XVII. A catalyst in which component A is a compound having the formula $MX_n$ bonded chemically through the fragment

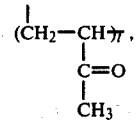

where t=100—2000 with the surface of a polymer carrier activated with an organometallic compound having the formula $M'R_pZ_{k-p}$. The catalyst of this type is shown schematically below:

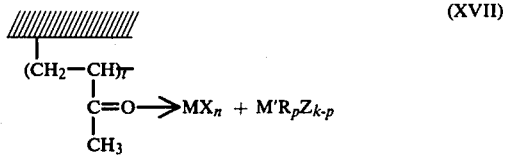

(XVII)

Some representatives of this catalyst are:

1. $TiCl_4$ applied onto the surface of polyethylene-gr.-polymethylvinylketone activated with $Al(C_2H_5)_2Cl$.

2. $VCl_4$ applied onto the surface of polystyrene-gr.-polymethylvinylketone activated with $Al(C_2H_5)_2Cl$.

3. $VCl_4$ applied onto the surface of polyethylene-gr.-polymethylvinylketone activated with $Al(iso-C_4H_9)_2H$.

XVIII. A catalyst in which component A is a compound having the formula $MX_n$ bonded chemically through the fragment

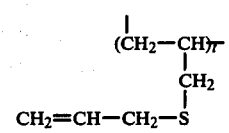

where t=4—9 with the surface of a polymer carrier activated with an organometallic compound having the formula $M'R_pZ_{k-p}$.

The catalyst can be described schematically as this:

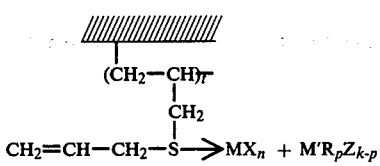

(XVIII)

Component A

Some representatives of this catalyst are:

1. $TiCl_4$ bonded chemically with the surface of polyethylene-gr.-polydiallylsulphide activated with $Al(C_2H_5)_2Cl$.

2. $VCl_4$ bonded chemically with the surface of polyethylene-gr.-polydiallylsulphide activated with $Al(C_2H_5)_2Cl$.

3. $VCl_4$ bonded chemically with the surface of polypropylene-gr.-polydiallylsulphide activated with $Al(C_2H_5)_2Cl$.

XIX. A catalyst in which component A is a compound having the formula $MX_n$, bonded chemically through the fragment

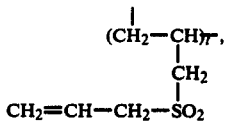

where t=4—9, with the surface of a polymer carrier activated with an organometallic compound having the formula $M'R_pZ_{k-p}$.

The catalyst of this type can be represented as follows:

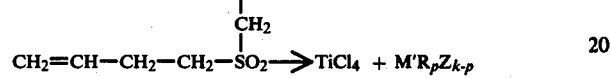

Component A

Representatives of this catalyst are the following compounds:

1. $TiCl_4$ bonded chemically with the surface of polyethylene-gr.-polydiallylsulphone activated with $Al(C_2H_5)_2Cl$.
2. $TiCl_4$ bonded chemically with the surface of polystyrene-gr.-polydiallylsulphone activated with $Al(C_2H_5)_2Cl$.

XX. A catalyst in which component B is an organometallic compound having the formula $M'R_pZ_{k-p}$ bonded chemically through the fragment

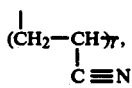

where t=500—2000, with the surface of a polymer carrier coupled with a compound having the formula $MX_n$.

The catalyst of this type can be described schematically as

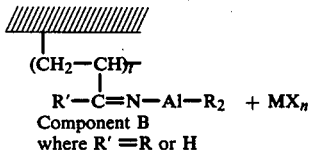

Component B
where R' =R or H

Representatives of this catalyst are:

1. $Al(C_2H_5)_3$ bonded chemically with the surface of polyethylene-gr.-polyacrylonitrile and coupled with $VCl_4$.
2. $Al(iso—C_4H_9)_2H$, bonded chemically with the surface of polypropylene-gr.-polyacrylonitrile coupled with $VCl_4$.

XXI. A catalyst in which component B is a compound having the formula $M'R_pZ_{k-p}$ bonded chemically through the fragment

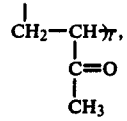

where t=100—200, with the surface of a polymer carrier coupled with a compound having the formula $MX_n$.

The catalyst of this type can be represented as

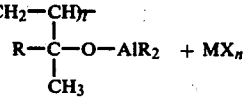

Component B

Representatives of this catalyst are:

1. $Al(C_2H_5)_3$ bonded chemically with the surface of polyethylene-gr.-polymethylvinylketone coupled with $VOCl_3$.
2. $Al(iso—C_4H_9)_3$ bonded chemically with the surface of polystyrene-gr.-polymethylvinylketone coupled with $VOCl_3$.

XXII. A catalyst containing component C which is a product of interaction of $MX_n$ and $M'R_pZ_{k-p}$, having the general formula $MR_mX_{n-m}$, where M, X, n, M', m, R, Z, p and k as specified above, bonded chemically through the fragment

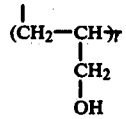

where t=4—9, with the surface of a polymer carrier.

The catalyst of this type can be represented schematically as follows:

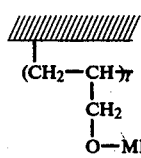

Some representatives of this catalyst are:

1. $Ti(CH_2C_6H_5)_4$ bonded chemically with the surface of polyethylene-gr.-polyallyl alcohol.
2. $V(CH_2C_6H_5)_4$ bonded chemically with the surface of polyethylene-gr.-polyallyl alcohol.

XXIII. A catalyst containing component C, which is a product of interaction of said $MX_n$ and $M'R_pZ_{k-p}$, having the formula $MR_mX_{m-n}$ bonded chemically through the fragment

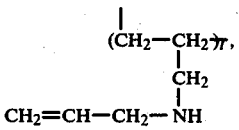

where t = 4— 9, with the surface of a polymer carrier.

The catalyst can be represented schematically as follows:

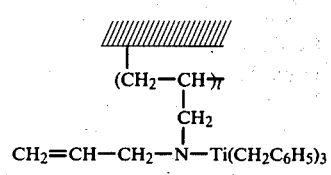 (XXIII)

The proposed catalyst for polymerization, copolymerization and oligomerization of olefins and diolefins can be prepared by the reaction of a suspension of a polymer carrier in hydrocarbon or halohydrocarbon solvents with one of the compound (or its solution) having the formula $MX_n$, $M'R_kZ_{k-p}$, or $MR_mX_{n-m}$, with susequent isolation by chemical methods of free products, and activation of the obtained component A with a compound having the formula $M'R_pZ_{k-p}$, or combination of the obtained component B and $MX_n$.

An example of application of $MX_n$ onto the surface of polymer carriers (preparation of component A of the catalyst) is the reaction of $VCl_4$, and also $Ti(OC_4H_9)_4$, with polyethylene-gr.-polyallyl alcohol:

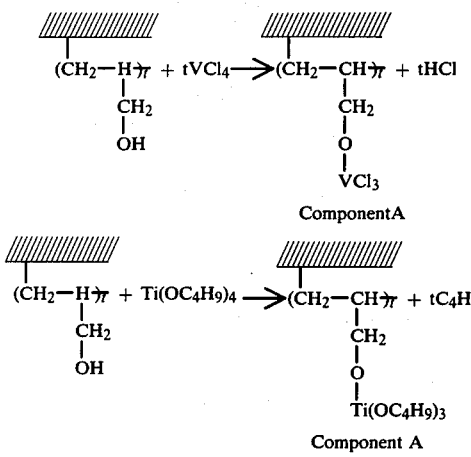

(XXIV)

Component A (XXV)

Component A

This is the path along which the reaction for preparing component A follows, provided $MX_n$ is chemically bonded with the surface of the polymer carrier through a fragment incorporating one of the following groups $\gamma$:

—OH, —NH$_2$, >NH, —COOH, R'NH, R'OH, or —CH$_2$SH.

It should be noted that in contrast to typical homogeneous catalysts on the basis of $(C_5H_5)_2TiCl_2$, $Ti(OC_4H_9)_4$ or $VO(OC_2H_5)_3$, activated with $M'R_pZ_{k-p}$, the proposed catalyst on the basis of these two compounds of transition metals (component A), activated with $M'R_pZ_{k-p}$, is a heterogeneous catalyst. If the fragment incorporates one of the functional groups Y: SR', COCH$_3$, CH$_2$SR', OCOCH$_3$, COOCH$_3$, C ≡ N, N(R')$_2$, —S, —SO$_2$R', —SOR'

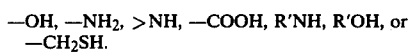

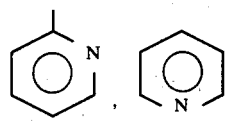

component A is formed by the donor-acceptor mechanism (formation of complex compounds). The diagram below shows a case where Y is C ≡ N:

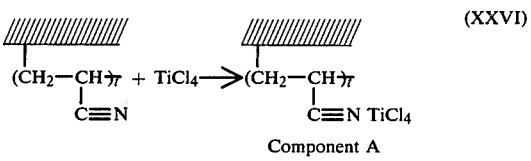

(XXVI)

Component A

Component B of the catalyst for polymerization and copolymerization of 1 olefins and diolefins is prepared by the reaction of a suspension of a polymer carrier and said fragment with $M'R_pZ_{k-p}$ (or its solution is a hydrocarbon solvent), for example, according to this diagram:

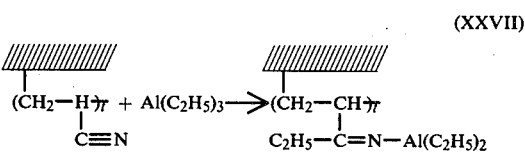

(XXVII)

The catalyst containing component C is obtained by the reaction of $MR_mX_{n-m}$ with a polymer carrier containing said fragments, for example as follows:

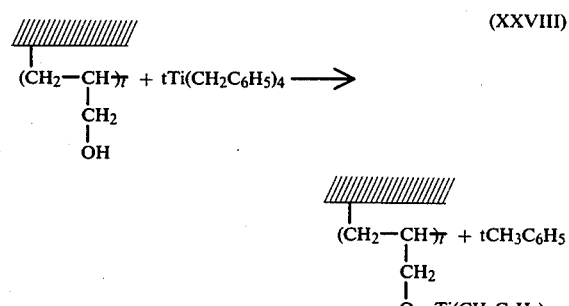

(XXVIII)

Carriers for catalysts for polymerization and copolymerization of olefins and diolefins are prepared as follos. Carbon-chain polymer is processed mechanochemically, with radiation, or by chemical action, in the presence of compounds having the formula

where R', R", R''' and Y are as specified above, in other words, compounds that contain double carbon-carbon bond on the one hand and a functional group capable of fixing $MX_n$, $M'R_pZ_{k-p}$, or $MR_mX_{n-m}$, on the other hand.

The double carbon-carbon bond is responsible for the graft polymerization of compounds having the formula

with formation of said fragments, while the method of initiating the polymerization is so selected that the grafting should be only done on the surface of the carrier-carbon-chain polymer, according to this diagram:

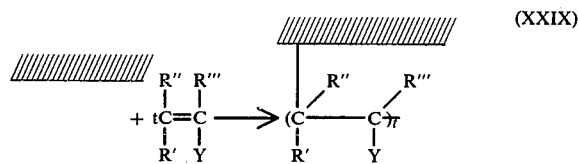

Most effective is graft-polymerization of compounds having the formula

onto the surface of carbon-chain polymers initiated by ionizing irradiation ($\delta$-radiation of $Co^{60}$ isotope, accelerated electrons, high-frequency discharge).

This method makes it possible to utilize carbon-chain polymer of any nature (including identical or close in nature to synthezised polymer) as a carrier for components A, B and C, to control effectively the density of grafted polymer chains and their mean degree of polymerization t. Moreover, this grafting to macromolecules of the superficial layer does not produce changes in the main bulk of the carbon-chain polymer, as a result of which the grafted fragments are localized only on the surface of the carrier.

The thus prepared carbon-chain polymers with grafted fragments can be used for application onto them of $MX_n$, $M'R_pZ_{k-p}$, or $MR_mX_{n-m}$, or the grafted fragments can undergo polymer-analogous transformations for preparing functional groups of a different nature (for example, hydrolysis of acetate groups to hydroxyl, reduction of ketone groups to hydroxyl groups, and of nitrile groups to amino groups).

The polymer-analogous transformation of grafted fragments on the surface of carbon-chain polymers occur with quantitative yield, without side processes under the suspension, and in relatively mild conditions, for example, according to the following diagram:

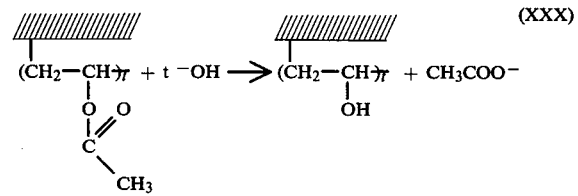

Compounds of the allyl type containing groups —OH, NH, —$NH_2$ (allyl alcohol, allylamine, diallylamine, allylmercaptan) are selected because owing to the high degradation transfer of the chain onto the monomer, they are referred to hardly polymerizing compounds. This, in turn, leads to the absence of homopolymers of the grafted compounds of the allyl type and also to the formation of only short (t =4 —9) polymer fragments.

This latter circumstance is most important, since owing to it sufficient steric accessibility for chemical binding of $MX_n$, $M'R_pZ_{k-p}$ or $MR_mX_{n-m}$ with functional groups of Y fragments is observed.

The catalyst for polymerization and copolymerization of olefins and diolefins, according to the invention, is formed by the reaction of component A with a compound having the formula $M'R_pZ_{k-p}$ (according to diagrams I through XIX). The molar ratio of M' in $M'R_pZ_{k-p}$ to M in component A is 5–500, preferably 10–100. The first step in the interconversions in the systems $MX_n$-$M'R_pZ_{k-p}$ is the formation of the active polymerization bond M—R. As component A reacts with $M'R_pZ_{k-p}$ the active center of polymerization also incorporates the metal-carbon bond M—R. However, depending on the nature of $MX_n$ and the fragments, this active bond can be localized on the surface of the polymer carrier, for example:

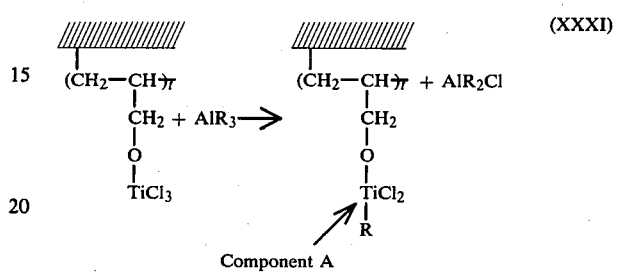

or the reaction of component A with $M'R_pZ_{k-p}$ may result in full or partial detachment of the transition metal from the surface of the carrier with the formation of active centers outside the polymer carrier:

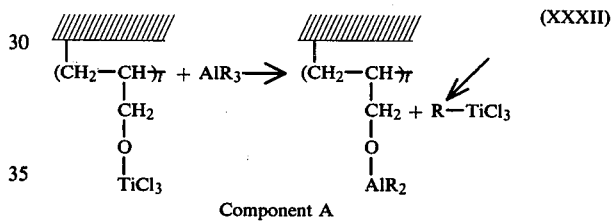

(The arrow indicates the most probable point of incorporation of the polymerizable monomer).

The catalyst for polymerization, copolymerization, and oligomerization of olefins and diolefins, in which component A is formed from $Ti(OC_4H_9)_4$ or $VO(OC_2H_5)_3$ on the said carrier, induces polymerization according to the diagram XXXI, while in case with the other compounds of transition metals, the polymerization occurs on both types of active centres (XXXI and XXXII).

Active centers arise similarly in a catalyst containing component B which is present in the combination with compound $MX_n$. In this case the molar ratio of M' in component B and M in $MX_n$ is 20–200, preferably 50–100. in the catalyst containing component C, the active bond M—R is present already in chemical bonding $MR_mX_{n-m}$ through fragment

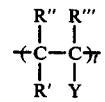

with the surface of the polymer carrier.

The catalyst for polymerization, copolymerization, and oligomerization of olefins and diolefins, according to the present invention, has the following advantages over the known catalysts used for the same purpose.

1. The proposed catalyst is 5-100 times more active then the known catalyst (with respect to the yield of the end product). The yield of polyethylene with the proposed catalyst can be as high as 1000 kg per gram of transition metal.

2. The high activity of the catalyst facilitates the otherwise labour-consuming operation of removing its residues from the obtained polymers, and in some cases this operation is not necessary at all, which all simplifies the flowsheet of the polymerization process.

3. The simplicity of using the proposed catalysts, consisting in that the obtained polymers become readily workable at the stage of their polymerization. They have high fluidity in the molten state, high bulk weight, and good physico-mechanical properties. Moreover, if $Ti(OC_4H_9)_4$ is used for preparing component A, the fluidity index for molten polyethylene, obtained at a pressure of 10 atmospheres, is 0.1–3.0 g/10 min, without using hydrogen as an agent controlling the molecular weight. If a catalyst in which component A contains a vanadium compound ($VCl_4$, $VO(OC_2H_5)_3$, $VOCl_3$) is used, it is sufficient to have 10–15 percent by volume of hydrogen in the gaseous state to obtain polyethylene having the index of melt fluidity of 10–12 g/10 min. The bulk weight of polyethylene powder obtained with the proposed catalyst can be as high as 530 g/liter.

4. The proposed catalysts, depending on the combination of the components and the conditions of the reaction, can be used to prepare low-molecular olefin oligomers having the degree of polymerization of 10–20, which can be used independently. The yield of liquid reaction products can be 500 kg per gram of transition metal.

5. The catalysts according to the invention can be effectively used to prepare olefin copolymers, and also copolymers of olefins with dienes having practically unlimited quantities of the starting monomers, and also polyolefin rubbers, for example, copolymers of ethylene with propylene and ethylene ethylidene norbornene, capable of further transformations. The fact that they can also be used in processes of oligomerization, widens even more the field of their application. The proposed catalysts can be considered all-purpose, from the aspect of the range of products that can be prepared with their use.

6. In contrast to the known catalysts on the basis of vanadium compounds, having unstable character at temperature of polymerization, i.e. at 20–40° C. (the rate of the process attains its maximum already after mixing the components of the catalyst, and then drops sharply), the proposed catalysts, whose component A incorporates one of the compounds $VCl_4$, $VOCl_3$, $VO(OC_2H_5)_3$, bonded chemically through the fragment $$\begin{array}{cc} R''' & R'' \\ | & | \\ C= & =C \\ | & | \\ R & Y \end{array}$$

with the surface of a carbon-chain polymer and activated with $M'R_pZ_{k-p}$, have stable character of their action in the course of the lengthy periods of time (several hours) even at elevated temperatures (80–90° C.). This markedly simplifies the equipment used in the polymerization process. No crystallization or fibrillation occur during the polymerization process.

7. The proposed catalysts contain, as carriers, polymers identical or close (with respect to their properties) to the obtained products. For this reason, the polymer carrier should not be removed from the end product, since it does not impair its properties.

8. The process for preparing the proposed catalysts is relatively simple. Polymers of any nature can be used for preparing the catalysts according to the invention. These may be polyolefins, copolymers of olefins, polydienes, polystyrene. The fragments through which $MX_n$, $M'R_pZ_{k-p}$ or $MR_mX_{n-m}$ are bonded chemically with the surface of carbon-chain polymers, are readily available materials. The process of their grafting onto the surface of carbon-chain polymers is simple, and can be effected by any known method of graft-polymerization.

The whole list of the above-named advantages can be attained with none of the known catalysts used for polymerization, copolymerization of olefins and diolefins.

The proposed catalysts for polymerization, copolymerization, and oligomerization of olefins and diolefins can be prepared both by batch and continuous processes, and can be used in the conditions of the existing and newly build plants manufacturing polyolefins and their copolymers by the low-pressure method.

For a better understanding of the invention, the following examples of its practical embodiment are given by way of illustration.

EXAMPLE 1

An upper part of a two-chamber glass ampoule (feeding chamber and reaction chamber) provided with separate thermostats is loaded with 4.1 g of low-pressure polyethylene (mol. weight 923,000, ash content 0.06%). The feeder chamber already contains 0.05 g of $CuCl_2$ (to prevent homopolymerization of vinyl acetate in the feeder chamber) and the whole ampoule is evacuated to $1 \times 10^{-3}$ mm Hg. Then 0.9221 g of pure and freshly distilled vinyl acetate is deposited and the ampoule is sealed. The radiation gas-phase grafting of vinyl acetate to polyethylene is initiated with a source of gamma radiation, radioactive isotope $Co^{60}$. The irradiation intensity 0.8 Mrad/hr is maintained constant throughout the whole experiment; the absorbed dose is 6.0 Mrad. The feed-chamber is protected from the radiation. After grafting, the obtained product — polyethylene-gr.-polyvinylacetate (4.9 g), — is washed with hot benzene, and dried in a vacuum drier to constant weight. The degree of grafting (weight percent of grafted vinyl acetate to the weight of the starting polyethylene) is 12.5 percent.

The radiation-chemical yield, determined as $$G_{(-M)} = \frac{N \times \Delta P \times 100}{6.24 \times 10^{13} D \times M(P_o \Delta P)\rho} \text{ mol/100 eV}$$

where N is the Avogadro number, $\Delta P$ is the weight of grafted monomer, D is absorbed dose (rad), M is the mol. weight of the monomer, $\rho$ density of the polymer, is $3 \times 10^2$ mole/100 eV.

The hydrolysis of the grafted fragments of vinylacetate is carried out as follows. A suspension consisting of 2.5 g of the obtained polyethylene-gr.-polyvinylacetate in methyl alcohol (100 ml) is heated and 0.3 g of sodium methylate in 20 ml of methyl alcohol is slowly added (in the course of two hours) with intense stirring. The hydrolyzed copolymer is washed with methyl alcohol and then several times with distilled water, and dried to constant weight. The yield is 2.2 g of a carrier for the catalyst for polymerization and copolymerization of olefins: — polyethylene-gr.-polyvinyl alcohol, containing 4.3 percent of hydroxy groups (determined by the Verley method) located only on the surface of polyethylene.

A three-neck flask provided with a reflux condenser, and a dividing funnel, is loaded with a suspension consisting of 1.5 g of the obtained hydrolyzed polyethylene-gr.-polyvinylacetate and 70 ml of pure and freshly distilled carbon tetrachloride. Then, at a temperature of 70° C., added to the flask is excess of $TiCl_4$ (0.5 g in 20 ml of $CCl_4$). The reaction terminates in three hours (test for gaseous HCl). The product of the reaction is transferred in an inert atmosphere into a vacuum filter, washed three times with 25–30 ml portions of HCl, and dried to constant weight, to prepare 1.3 g of light yellow powder containing 64 mg of Ti/g product — component A of the catalyst for polymerization, copolymerization and oligomerization of olefins and diolefins.

The process of polymerization, copolymerization and oligomerization of olefins and diolefins is carried out in a thermally controlled reactor, manufactured out of stainless steel with intense stirring of the reaction mixture ($\approx$1500 r.p.m.) with the aid of a shielded motor, and a paddle stirrer. The reactor is dried at a temperature of 60° C. in vacuum and blown with ethylene. The reactor is loaded as follows. First 0.05 g of the obtained product is loaded into the reactor having the capacity of 1.0 liter, in an inert atmosphere. The reactor is then evacuated to $1 \times 10^{-2}$ mm Hg, and loaded into it are 200 ml of pure and freshly distilled n-heptane. A temperature of 70° C. is maintained in the reactor with the aid of a thermostat. Ethylene is added from a special measuring cylinder in the quantity required to ensure the desired pressure inside the reactor (10 atm), and finally the co-catalyst (activator) $(C_2H_5)_2AlCl$ (0.96 g) is introduced from a syringe (batcher).

The polymerization process is continued for three hours at constant pressure which is attained by continuous delivery of ethylene into the reactor as it is consumed in the polymerization process. The reaction is stopped by adding 20 ml of ethyl alcohol after which the pressure inside the reactor is dropped to 1 atm, the reaction product is unloaded, the solvent is removed from it, the product is dried to constant weight, and weighed. The yield of high-molecular crystalline polyethylene is 39 g (12 kg/g Ti).

EXAMPLE 2

Under conditions similar to those described in Example 1, the reactor is loaded with 0.06 g of $TiCl_4$ bonded chemically with the surface of hydrolyzed polyethylene-gr.-polyvinylacetate and 0.64 g of $Al(C_2H_5)_3$. The polymerization is continued for four hours to give 15.5 g of high-molecular crystalline polyethylene (4 kg/g Ti).

EXAMPLE 3

Under conditions similar to those described in Example 1, vinylacetate (0.4 g) is grafted to polypropylene powder (4.2 g). The yield is 4.5 g of polymer carrier for the catalyst of polymerization. It is hydrolyzed in the same conditions as described in Example 1, except that o-xylene is used as the solvent and the temperature is maintained at 85°–90° C.

1.4 g of the obtained hydrolyzed polypropylene-gr.-polyvinylacetate interacts with 0.6 g of $VCl_4$ as in Example 1 in a solution of carbon tetrachloride. The yield of light-brown product containing 2.15 percent of vanadium (component A) is 1.3 g.

Under conditions of Example 1, the reactor is loaded with 0.14 g of the obtained product and 0.64 g of $(C_2H_5)_2AlCl$. The polymerization process is continued for three hours. The yield of polyethylene is 31.5 g, which corresponds to the yield of 10.5 kg/g V. The polymer is characterized by the content of 0.19 double bonds per 1000 carbon atoms, 60 per cent of them having vinyl and 40 per cent vinylidene (in the absence of trans-vinylene) saturation. The physico-mechanical tests have shown that the polymer is characterized by the yield point of 245 kg/sq.cm, neck length 1.3, tensile strength 350 kg/sq.cm, elongation at break over 200 per cent.

EXAMPLE 4

Under conditions of Example 1, to 17.4 g of polyethylene-powder 1.1 g of vinylacetate is grafted, 5.9 g of the product is hydrolyzed as in Example 1, to prepare 5.1 g of hydrolyzed polyethylene-gr.-polyvinylacetate. Under conditions of Example 1, reacted are 2.4 g of the obtained carrier in a suspension of 200 ml of toluene and 0.1 g of $(C_5H_5)_2TiCl_2$ to prepare 2.3 g of light pink powder containing 0.54 mg of Ti/g of the product, component A of the catalyst for polymerization. The polymerization is continued in benzene in conditions as specified in Example 1. The reactor is loaded with 0.45 g of $(C_5H_5)_2TiCl_2$ bonded chemically with the surface of hydrolyzed polyethylene-gr.-polyvinylacetate and 0.28 g of $(iso-C_4H_9)_2AlCl$. The polymerization is carried out for four hours to prepare 7.5 g of high-molecular polyethylene (30 kg/g Ti).

EXAMPLE 5

Under conditions of Example 1 reacted in benzene are 2.4 g of hydrolyzed polyethylene-gr.-polyvinylacetate, obtained in Example 4, and 0.94 g of $Ti(OC_4H_9)_4$, to prepare powder whose colour is the same as that of the starting polymer. The powder contains 0.74 mg of Ti/g of the product. The polymerization is carried out in benzene as in Example 1. The reactor is loaded with 0.49 g of the obtained product and 0.3 g of $Al(C_2H_5)_2Cl$. The polymerization is continued for four hours to give 16 g of polyethylene (44 kg/g Ti). The index of melt fluidity is 0.3412 g/10 minutes.

EXAMPLE 6

Vinylacetate (0.34 g) is grafted to polystyrene (1.7 g) having the molecular weight of 35,000 as in Example 1, except that the irradiation intensity is 1.0 Mrad per hour, the absorbed dose of gamma radiation is 4.5 Mrad. The yield is 1.9 g, the degree of grafting is 20 percent. The hydrolysis is carried out as in Example 1, to obtain 1.6 g of polymer carrier. The carrier then reacts with excess $TiCl_4$ to prepare 1.4 g of component A of the catalyst of polymerization, copolymerization and oligomerization of olefins and diolefins, containing 68 mg Ti/g of the product. The reactor is loaded with 0.0428 g of this product and 0.96 g of $(C_2H_5)_2AlCl$ to prepare 29 g of polyethylene (10 kg/g of Ti).

EXAMPLE 7

Vinylacetate (1.3 g) is grafted to a copolymer of ethylene with propylene (7.8 g) containing 1.4 mole percent of propolylene links, as described in Example 1. After hydrolysis, 3.4 g of the obtained poly(ethylene-co-propylene)-gr.-polyvinylacetate, 3.1 g of hydrolyzed copolymer are obtained which react with 0.94 g of $VOCl_3$, as described in Example 1, to prepare 3.0 g of brown powder containing 54.1 mg V/g. In polymerization with 0.071 g of this product and 0.950 g of $(C_2H_5)_2AlCl$, 43 g of polyethylene are prepared (14 kg/g V).

EXAMPLE 8

A reactor is loaded with 0.6 g of $VOCl_3$ bonded chemically with hydrolyzed poly(ethylene-co-propylene)-gr.-polyvinylacetate obtained in Example 7, and containing 54.1 mg/of V/g and 0.66 g of $(C_2H_5)_2AlCl$. The composition of the gaseous mixture delivered to the polymerization is as follows: ethylene 65.4 percent by volume, propylene 34.6 percent by volume, the total pressure in the reactor being 5.0 atm. The copolymerization is continued for one hour. The yield of elastic, rubber-like copolymer containing 45 mole percent of propylene and 55 mole percent of ethylene is 24 g. Its total unsaturation is 1.0 double bond per 1000 carbon atoms (50 percent of vinylidene, 30 percent of trans-vinylene, and 20 percent of vinyl bonds). The physico-mechanical tests have shown that the polymer can be referred to the class of rubber-like ethylene-propylene polymers (S -figurative extension curve); tensile strength is 120 kg/sq.cm., elongation over 330 percent.

EXAMPLE 9

Methyvinylketone (3.0 g) is grafted to polyethylene powder (70 g) having the specific surface is 1.6 sq.m per gram, in conditions as described in Example 1. The irradiation intensity is 0.15 Mrad/hr (42 roentgen per sec) and it is maintained constant for ten hours. The absorbed dose of gamma radiation is 1.5 Mrad. After grafting, the product is kept in benzene for 27 hours to remove homopolymer of polymethylvinylketone that may remain in the product, passed through a filter, and dried in a vacuum drier at 80° C. to constant weight. The grafting degree is 4.2 percent; the radiation-chemical yield is $4 \times 10^2$ molecules/100 eV. The infra-red spectrum of polyethylene-gr.-polyethylvinylketone, in addition to the main bands of polyethylene, contains also an intense absorption band at 1728 $cm^{-1}$, which is due to the valence oscillations of the carbonyl group of the grafted fragments.

Carbonyl groups are reduced to hydroxyl groups as follows.

A suspension consisting of 150 ml of pure freshly distilled cyclohexane and 30 g of polyethylene with grafted polymethylvinylketone, are placed in an argon atmosphere into a three-neck flask provided with a reflux condenser and a dividing funnel. At temperature of 60° C. and with intense stirring, 50 ml of ether suspension of $LiAlH_4$ (12 g of $LiAlH_4$) are added in drops from a dividing funnel in the course of one hour. The reaction mixture is kept for further 60 minutes at this temperature with stirring and then excess $LiAlH_4$ is removed and 50 ml of a 10 percent HCl are added. The polymer is rinsed successively with water, alcohol, and petroleum ether at 80° C. and 1 mm Hg for 14 hours. The analysis of the infra-red spectra of the obtained polymer shows that the reduction of the carbonyl groups is almost complete: in addition to a very weak absorption band at 1725 $cm^{-1}$, a wide and intense band with the maximum at 3445 $cm^{-1}$ is observed, which is due to the valence oscillations of hydroxyl group. The polymer has the following structure

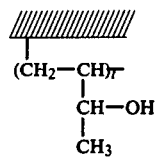

The OH-group content (determined by the Verley method) is 1.47 percent. They are located only on the surface of polyethylene. The compound of the transition metal is fixed chemically on the surface of such a polymer carrier (preparing component A) by a procedure described in Example 1. The suspension containing 4.1 g of the reduced polyethylene-gr.-polymethyvinylketone in 100 ml of $CCl_4$ is reacted with 0.9 of $VCl_4$ in 30 ml of $CCl_4$, at a temperature of 70° C., for three hours. The product is filtered in an inert atmosphere, washed to remove free components, and dried on a vacuum filter, to prepare 4.0 g of light brown powder containing 17.5 ml of V/g -component A of the catalyst.

The reactor of the polymerization plant is loaded in conditions of Example 1 with 0.1192 g of the obtained product. 150 ml of benzene as solvent, and 0.5288 g of $Al(C_2H_5)_2Cl$.

The polymerization is continued for three hours. The yield of high-molecular crystalline polyethylene is 36 g (18 kg/g V).

EXAMPLE 10

A reactor of 0.5 liter capacity is loaded under conditions described in Example 1, with 150 ml of n-heptane, 0.062 g of a product obtained by in Example 9, and 0.3966 g of $Al(C_2H_5)_2Cl$. The polymerization is continued for five hours. The yield of linear polyethylene (the molecular weight 2,880,000) is 15 g (17.2 kg/g V).

EXAMPLE 11

The reactor is loaded under conditions of Example 10 with 0.050 g of the product obtained in Example 9, and 0.3966 g of $Al(C_2H_5)_2Cl$. In order to control the molecular weight of the formed polyethylene, 10 vol.% of hydrogen is introduced into the reactor. The yield of polyethylene is 13.0 g (15 kg/g V). The molecular weight is 474,000.

EXAMPLE 12

Under conditions of Example 10, to control the molecular weight of the polymer, 30 vol.% of hydrogen is introduced into the reactor. 0.0663 g of the product obtained in Example 9 and 0.4 g of $Al(C_2H_5)_2Cl$ are reacted to give 11.5 g of polyethylene (10 kg/g V). The molecular weight is 186,000.

EXAMPLE 13

Under conditions of Example 10, reacted are 0.0635 g of the product prepared in Example 5, and 0.4 g of $Al(C_2H_5)_2Cl$. The composition of the gaseous mixture: hydrogen, 40 vol.%, ethylene, 60 vol.%. The yield of polyethylene is 12.7 g (11.0 kg/g V).

The molecular weight is 88,800.

EXAMPLE 14

Under conditions of Example 10, reacted are 0.0669 g of the product obtained in Example 9 and 0.4 g of $Al(C_2H_5)_2Cl$. The gaseous composition: 50 vol.% of hydrogen and 50 vol.% of $C_2H_4$. The yield of polyethylene is 5.5 g (4.6 kg/g of V). The molecular weight is 59,600.

EXAMPLE 15

Under conditions of Example 10, reacted are 0.1034 g of the product obtained in Example 19, 150 ml of benzene, and 0.4 g of Al($C_2H_5$)$_2$Cl, to obtain 25 g of high-molecular polyethylene (14 kg/g V).

EXAMPLE 16

Reacted are 4.03 g of reduced polyethylene-gr.-polymethylvinylketone obtained in Example 9 and 15 ml of a 10.47% solutioh of VCl$_4$ in CCl$_4$, to prepare 4.0 g of brown-yellow powder containing 12.8 mg V/g - component A of the catalyst of polymerization. Under conditions of Example 10, reacted are 0.1372 g of the obtained product and 0.4 g of (iso-$C_4H_9$)$_2$AlCl, to prepare 16 g of linear polyethylene (10kg/g V).

EXAMPLE 17

Mesityl oxide (4-methyl-3-pentene-2-one) is grafted to polyethylene powder as in Example 9. To 30.0 g of polyethylene grafted are 2.5 g of mesityl oxide (irradiation intensity is 1.0 Mrad/hour; absorbed dose 60 Mrad). After grafting, the product is placed in benzene and kept for 24 hours, then filtered, and dried to constant weight, to obtain 30.5 g of polyethylene-gr.-poly(4-methyl-3-pentene-2-one). The grafting degree is 16 percent, the radiation-chemical yield is 3 mole/100 eV. Carbonyl groups in 3.3 g of the obtained polymer are reduced as in Example 9. As 3.2 g of the reduced polyethylene-gr.-poly(ethylene-gr.-methyl-3-pentene-2-one) are processed with 0.4 g of TiCl$_4$, as in Example 16, 3.2 g of light brown product containing 2.1 mg of Ti/g are obtained.

Under the conditions of Example 10, 0.4 g of the obtained product and 0.4 g of Al($C_2H_5$)$_2$Cl are reacted to obtain 8.5 g of high-molecular linear crystalline polyethylene (10.1 kg/g Ti).

EXAMPLE 18

To a suspension consisting of 5 g of reduced polyethylene-gr.-polyvinylketone, obtained in Example 9, and 40 ml of pure freshly distilled benzene, added in an inert atmosphere is 0.3 g of ($C_5H_5$)$_2$TiCl$_2$ dissolved in 130 ml of benzene. The reaction mixture is then heated to 60°– 70° C. and the reaction is continued for two hours with intense stirring. After filtration and triple washing with benzene (50-ml portions) obtained are 4.9 g of pale yellow powder containing 0.46 mg of Ti/g of the product (component A of the catalyst of polymerization). In conditions of Example 10 reacted are 0.4163 g of the obtained product, 150 ml of toluene and 0.4 g of Al($C_2H_5$)$_2$Cl. The polymerization is continued for three hours to give 3.5 g of polyethylene (18 kg/g Ti).

EXAMPLE 19

Methylvinylketone (0.5 g) is grafted to polystyrene (7.4 g) under the conditions of Example 1 (irradiation intensity is 0.6 Mrad/hr; absorbed dose is 4.2 Mrad). 3.2 g of the obtained polystyrene-gr.-polymethyldinylketone are reduced with LiAlH$_4$ as in Example 9, to obtain 2.9 g of reduced polystyrene-gr.-polymethylvinylketone, which are reacted with 2.04 g of Ti(OC$_4$H$_9$)$_4$ in benzene. The obtained product is a powder (3.0 g) the colour of which does not differ from that of the starting polymer. It contains 1.1 mg of Ti/g of the product.

The reactor is loaded with 0.6576 g of the obtained product and 0.5288 g of Al($C_2H_5$)$_2$Cl, and the reaction is carried out in conditions of Example 9 to prepare 14.8 g of polyethylene (21 kg/g Ti).

EXAMPLE 20

As in Example 19, the reactor is loaded with 0.49 g of the product of interaction of Ti(OC$_4$H$_9$)$_4$ with reduced polystyrene-gr.-polymethylvinylketone, and 0.3 g of Al(iso-$C_4H_9$)$_2$Cl. The yield is 14 g of high-molecular crystalline polyethylene (28 kg/g Ti).

EXAMPLE 21

Under the conditions of Example 1, allyl alcohol (1.106 g) is grafted to polyethylene powder of high density (9.2 g). The irradiation intensity is 1.2 Mrad, and it is maintained constant for 20 hours (the absorbed dose of gamma radiation is 24 Mrad). The product is washed with benzene. The yield is 9.4 g of polyethylene-gr.-polyallyl alcohol. In addition to absorption bands characteristics of polyethylene, the infra-red spectrum of the product also has a wide band of medium intensity with a maximum at 3480 cm$^{-1}$, which is due to the valency oscillations of hydroxyl groups. The OH group content, as determined by the Verley method, is 0.86 percent. The interaction of TiCl$_4$ with the obtained polymer is carried out as described in Example 1. 4 g of polyethylene-gr.-polyallyl alcohol in 100 ml of CCl$_4$ are reacted with 0.5 g of TiCl$_4$ to prepare 3.9 g of light brown powder containing 3 mg of Ti/g of the product.

The polymerization is carried out as described in Example 1. A reactor is loaded with 2.0 g of the obtained product and 1.06 g of Al($C_2H_5$)$_2$Cl. The yield is 72.0 g (12 kg/g Ti) of linear high-molecular crystalline polyethylene with the total unsaturation (number of double bonds per 1000 carbon atoms) 0.20. The yield point is 260 kg/sq.cm, the tensile strength 330 kg/sq.cm elongation at break 360 percent.

EXAMPLE 22

Under the conditions of Example 1, 1.1 g of allyl alcohol is grafted to 7.1 g of polystyrene (irradiation intensity 1.0 Mrad/hr, the absorbed dose 10 Mrad) to obtain 7.0 g of polystyrene-gr.-polyallyl alcohol containing 0.18 percent of the OH groups. It is processed with VOCl$_3$ solution, as in Example 1, to prepare 6.8 g of brown powder containing 3.5 V/g of the product. Ethylene is polymerized with this product as described in Example 1. The reactor is loaded with 0.28 g of the obtained product and 0.8 g of Al($C_2H_5$)$_2$Cl to obtain 25 g of polyethylene (25 kg/g V) having the following properties: total unsaturation 0.20, yield point 200 kg/sq.cm, tensile strength 270 kg/sq.cm, elongation at break 380 percent.

EXAMPLE 23

Under conditions of Example 1, reacted are 0.7 g of the product obtained in Example 21 and 0.4 g of Al(iso-$C_4H_9$)$_2$Cl to prepare 34 g of polyethylene (17 kg/g Ti) having the following physico-mechanical characteristics: total unsaturation 0.30, yield point 180 kg/sq.cm, tensile strength 250 kg/sq.cm, elongation at break 440 percent.

EXAMPLE 24

An ampoule for gas-phase radiation grafting polymerization is loaded with 70 g of polyethylene powder having the specific surface of 1.6 sq.m/g and 5 ml of allyl alcohol. The radiation intensity is 1.25 Mrad/hr, the exposure is 48 hours. The process is similar to that described in Example 21. The yield is 69.2 g of polyethylene-gr.-polyallyl alcohol containing 0.71 percent of OH groups. To a suspension consisting of 7 g of the obtained polymer in 150 ml of $CCl_4$, added in an inert atmosphere are 15 ml of a 10 percent solution of $TiCl_4$ in $CCl_4$. The reaction is continued for three hours at 65°-70° C. After treating the product as in Example 1, 6.8 g of light brown product containing 1.5 mg of Ti/g are obtained. The reactor is loaded with 0.1527 g of the obtained product and 0.4 g of $Al(C_2H_5)_2Cl$. The yield is 9.6 g of polyethylene (42.5 kg/g of Ti).

EXAMPLE 25

Into a polymerization reactor, containing the catalyst consisting of 0.2243 g of the product obtained in Example 24 and 0.4 g of $Al(C_2H_5)_2Cl$, is delivered gaseous mixture consisting of 60 vol.% of ethylene and 40 vol.% of propylene. The reaction is continued for four hours and the yield is 8 g of elastic copolymer of ethylene and propylene (24 kg/g Ti).

EXAMPLE 26

Reacted are 6 g of polyethylene-gr.-polyallyl alcohol obtained in Example 24, in a medium of $CCl_4$, and 15 ml of a 6 percent solution of $VCl_4$ in $CCl_4$. The product is processed as in Example 1 to prepare 5.7 g of dark brown product containing 8 mg V/g. A reactor is loaded with 0.251 g of the obtained product, 150 ml of n-heptane, ethylene (to pressure of 10 atm) and 0.3 g of $Al(C_2H_5)_2Cl$. The polymerization is continued for two hours to prepare 108 g of high-molecular crystalline polyethylene (55 kg/g V).

EXAMPLE 27

Gas-phase polymerization of ethylene is carried out with 0.1773 g of the product obtained in Example 26 as a catalyst, and 0.3 g of $Al(C_2H_5)_2Cl$ in 5 ml of n-heptane. The polymerization is continued for one hour to give 38 g of high-molecular polyethylene (14 kg/g V).

EXAMPLE 28

An autoclave having the capacity of 1.5 liter and provided with a paddle agitator is loaded with 0.5 liter of hexane as a solvent, 0.227 g of the product obtained in Example 26, and 0.5 g of $Al(iso-C_4H_9)_2H$. The polymerization is carried out at a temperature of 70°-75° C., the composition of the gaseous mixture is: ethylene 70 vol%, hydrogen 30 vol.%. The reaction is continued for two hours. The yield is 80 g of polyethylene (43.5 kg/g V).

EXAMPLE 29

Under conditions of Example 28, an autoclave is loaded with 0.15 g of the product obtained in Example 26 and 0.4 g of $Al(iso-C_4H_9)_2H$. The composition of the gaseous mixture: ethylene 90 vol.%, hydrogen 10 vol.%, the total pressure in the reactor is 15.5 atm. The polymerization is continued for two hours to prepare 72 g of polyethylene (60 kg/g V); the index of melt fluidity is 2.18 g/10 minutes.

EXAMPLE 30

The autoclave is loaded with 0.1 g of the product obtained in Example 26, 150 ml of benzene recovered after polymerization (b.p. 68° C.), and 0.15 g of $Al(C_2H_5)_2Cl$. The polymerization is continued for one hour at a temperature of 80° C. and a pressure of ethylene of 4 atm. The yield of polyethylene is 15.7 g (19 kg/g V).

EXAMPLE 31

A reactor having the capacity of 0.8 liter is loaded with 0.4 g of benzine (b.p. 68° C.) recovered after polymerization, 0.3021 g of the product obtained in Example 26, and 0.5 g of $Al(C_2H_5)_2Cl$. The polymerization is continued for one hour under a pressure of ethylene of 4 atm. The yield of high-molecular (mol. wt. 1,648,000) polyethylene (having the bulk weight of 531 g/l, ash content 0.03 percent) is 86 g.

EXAMPLE 32

Polyethylene-gr.-polyallyl alcohol obtained by grafting 3 ml of allyl alcohol to 14 g of polyethylene, and containing 0.56 percent of OH groups, is reacted with $VO(OC_2H_5)_3$ as in Example 22 to prepare 13.7 g of light yellow powder containing 2.8 mg V/g of product.

A reactor having the capacity of 1.3 liter is loaded with 0.6358 g of the obtained product, 250 ml of n-heptane, and ethylene (to bring the total pressure to 12.5 atm), and polymerization is continued for one hour at a temperature of 90° C. to prepare 48 g of polyethylene (30 kg/g V).

EXAMPLE 33

The polymerization is done with the product obtained in Example 32 (0.5273 g) and $Al(C_2H_5)_2Cl$ (0.4 g), at a temperature of 70° C., for one hour and a pressure of ethylene of 10 atm, using 150 ml of benzene as solvent. The yield is 86.9 g of polyethylene (64 kg/g V), having the bulk weight of 311 g/liter, ash content 0.02 percent.

EXAMPLE 34

An autoclave is loaded with 0.138 g of the product prepared in Example 32, 0.26 g of $Al(C_2H_5)_2Cl$ and 100 ml of benzine. The pressure of ethylene is 3 atm, the polymerization temperature is 70° C., the duration of the process is one hour. The yield is 8.1 g of polyethylene (20.7 kg/v V).

EXAMPLE 35

An autoclave is loaded, under conditions of Example 34, with 0.155 g of the product obtained in Example 32 and 0.1 g of $Al(C_2H_5)_2Cl$, at a temperature of 80° C., and ethylene pressure of 4 atm. The polymerization is continued for one hour to give 13 g of polyethylene (29.6 kg/g V).

EXAMPLE 36

A reactor having the capacity of 0.5 liter is loaded with 0.2814 g of the product prepared in Example 32, 250 ml of benzine, and 0.5 g of $Al(C_2H_5)_2Cl$. A gaseous mixture consisting of 7 percent by volume of propylene and 93 percent by volume of ethylene is copolymerized under a total pressure of 4 atm. Introduced into the reactor in the course of the process, in equal portions, are 2 ml of pure ethylidene norborene (3 ml in 10 ml of benzene). The process is continued for 30 minutes. The yield of triple copolymer — ethylene-propylene-ethylidene norbornene, — is 14 g (17 kg/g V). The product (powder) is highly unsaturated (in the infra-red spectrum there is an intense band at 1640 $cm^{-1}$, weak bands at 880 and 910 $cm^{-1}$).

EXAMPLE 37

Under the conditions of Example 36, ethylene is co-polymerized with propylene and ethylidene norbornene in the ratio of the components of 50:60 (ethylene:propylene) in the presence of 3 ml of ethylidene norbornene. The catalyst is 0.34 g of the product obtained in Example 32 and 0.4 g of $Al_2(C_2H_5)_3Cl_3$. The yield of high-molecular rubber-like triple copolymer is 13 g. The copolymer is highly unsaturated.

EXAMPLE 38

Allyl alcohol (0.9 g) is grafted to polyethylene (8.3 g) after its treatment with a high-frequency discharge. The resultant product is polyethylene-gr.-polyallyl alcohol containing 0.72 percent of OH groups. 3.4 g of this product are reacted under the conditions of Example 1 with 0.8 g of $MoCl_5$ to prepare 3.3 g of light-brown powder containing 23 mg of Mo/g.

The polymerization is carried out as in Example 1; the catalyst in the reaction is 0.4076 g of the obtained product and 0.25 g of $Al(C_2H_5)_2Cl$. The yield of high-molecular polyethylene is 14.5 g (1.5 kg/g Mo).

EXAMPLE 39

4.9 g of polyethylene-gr.-polyallyl alcohol obtained in Example 38 are reacted with 1.1 g of $WCl_6$. The resultant product is brown powder containing 42.1 mg W/g. The yield is 5.0g. Ethylene is polymerized as described in Example 1, with 0.05 g of the obtained product and 0.6 g of $Al(iso-C_4H_9)_2Cl$. The yield of polyethylene is 3.4 g (1.7 kg/g W).

EXAMPLE 40

Ethylene is polymerized as in Example 1, except that benzene is used as solvent. The catalyst used in the reaction is 0.25 g of the product obtained in Example 26 and 0.95 g of $Zn(CH_3)_2$. The yield of polyethylene is 8.5 g (4.2 kg/g V).

EXAMPLE 41

Under the conditions of Example 1, ethylene and alpha-butene are copolymerized. This is done by delivering into a reactor a gaseous mixture containing 97 percent by volume of ethylene and 3 percent by volume of alpha-butene. The catalyst used in the reaction is 0.2 g of the product obtained in Example 26 and 0.64 g of $Al(C_2H_5)_2Cl$. The yield of the copolymer of ethylene with butene is 33 g (20 kg/g V); the product contains 1.7 $CH_3$ groups per 1000 carbon atoms.

EXAMPLE 43

In under the conditions of Example 1 reacted in toluene are 8.9 g of polyethylene-gr.-polyallyl alcohol, obtained in Example 24, and 0.2 g of $(C_5H_5)_2TiCl_2$. The yield is 8.8 g of yellowish substance containing 0.5 mg Ti/g. A reactor is loaded with 0.4 g of the obtained product and 0.64 g of $Al(C_2H_5)_2Cl$.

The polymerization is carried out in conditions of Example, except that 200 ml of benzene are used as the solvent. The yield of polyethylene is 6 g (30 kg/g Ti).

EXAMPLE 44

Component A of the catalyst of polymerization is prepared by reacting, in benzene, 9 g of polyethylene-gr.-polyallyl alcohol, obtained in Example 24 and Ti-$(OC_4H_9)_4$, (2 ml in 10 ml of benzene). The reaction is effected as in Example 1, except that 200 ml of benzene are used as the solvent. The catalyst used in the reaction is 0.985 g of the obtained product and 0.4 g of $Al(C_2H_5)_2Cl$. The polymerization is continued for three hours to prepare 50.5 g of polyethylene (84 kg/g Ti). The molecular weight of the product is 668,000.

EXAMPLE 45

The polymerization is effected with 0.4 g of the product obtained in Example 44 as the catalyst, and the process conditions are the same, except that the polymerization is continued for four hours. The yield of polyethylene is 30.2 g (112 kg/g Ti). The index of melt fluidity is 0.487 g/10 minutes; the bulk weight is 240 g/liter.

EXAMPLE 46

Under the conditions of Example 44 are reacted 0.2368 g of the product obtained in Example 44 and 0.4 g of $Al(C_2H_5)_2Cl$. The yield of polyethylene is 20.0 g (125 kg/g Ti).

EXAMPLE 47

Under the conditions of Example 24, 0.9 g of allyl alcohol is grafted to 18.0 g of polyethylene. The obtained product is reacted with 1.5 ml of $Ti(OC_4H_9)_4$ under the conditions specified in Example 44. The resultant product is a white powder (17.8 g) containing 0.25 mg of Ti/g. The polymerization with this product is carried out in conditions described in Example 44 for four hours. A reactor is loaded with 0.62 g of the obtained product and 0.4 g of $Al(C_2H_5)_2Cl$. The yield of the polyethylene is 37 g (250 kg/g Ti). The index of melt fluidity is 0.338 g/10 minutes.

EXAMPLE 48

Under the conditions of Example 47, the reactor of the polymerization plant is loaded with 0.712 g of the product obtained in Example 47 and 0.4697 g of $Al_2(C_2H_5)_3Cl_3$. The yield of low-molecular polyethylene is 27.7 g (160 kg/g Ti). The fluidity of the melt is very high (without load).

EXAMPLE 49

Under conditions of Example 47 (except that the temperature is 90° C.) the reactor is loaded with 0.65 g of the product obtained in Example 47 and 0.4 g of $Al(C_2H_5)_2Cl$. The yield of polyethylene is 46.0 g (290 kg/g Ti). The bulk weight of the product is 185 g/liter, intrinsic viscosity in tetraline at 135° C. is 0.35, the index of melt fluidity is 3.0 g/10 minutes.

EXAMPLE 50

Under the conditions of Example 47, the polymerization reactor is loaded with 0.27 g of the product obtained in Example 47 and 0.2 g of $Al(C_2H_5)_2Cl$. The polymerization is carried out under ethylene pressure of 30 atm for seven hours. The yield of polyethylene is 68 g (1015 kg/g Ti). The index of melt fluidity is 0.116.

EXAMPLE 51

Under the conditions of Example 47, the polymerization reactor is loaded with 0.542 g of the product obtained in Example 47 and 0.4 g of $AlC_2H_5Cl_2$. The reaction products are liquid oligomers. They are washed with a 10 percent solution of KOH, then with water, and separated on a dividing funnel. The solvent is distilled in vacuum. The yield of oligomers (a mixture of linear olefins, waxes, and also products of benzene alkylation with them) is 24 g (177 kg/g Ti).

EXAMPLE 52

Under the conditions of Example 51 (except that the pressure of ethylene is 30 atm), the reactor is loaded with 0.7185 g of the product obtained in Example 47 and 0.5 g of $AlC_2H_5Cl_2$. The yield of oligomers, which are products similar to those obtained in Example 51, is 81.8 g (432 kg/g Ti).

EXAMPLE 53

Under the conditions of Example 52, a reactor is loaded with 1.1 g of the product obtained in Example 47, and 0.8 g of $AlC_2H_5Cl_2$. The yield of oligomer having the same structure as in Example 51 is 138 g (505 kg/g Ti).

EXAMPLE 54

To polypropylene powder (6.3 g), crotyl alcohol is grafted (γ-methylallyl alcohol). The irradiation intensity is 1.0 Mrad/hour, the exposure is 48 hours. Processing of the obtained polypropylene-gr.-polycrotyl alcohol with $TiCl_4$ in conditions of Example 1 gives 6.0 g of light brown powder containing 0.4 mg Ti/g. The polymerization with said product (0.5 g) activated with 0.4 g of $Al(C_2H_5)_2Cl$ is carried out in conditions of Example 47. The yield of high-molecular polyethylene is 6.0 g (30 kg/g Ti).

EXAMPLE 55

To polyethylene powder (4.7 g) is grafted cinnamic alcohol (0.3 g), and the obtained product is processes in conditions of Example 1, with 0.8 g of $TiCl_4$, to prepare 4.5 g of light brown powder containing 0.38 g of Ti/g. The polymerization of ethylene is carried out with 0.8 g of the product obtained and 0.96 g of $Al(C_2H_5)_2Cl$ as the catalyst in conditions of Example 47, to prepare 4.2 g of polyethylene (14 kg/g Ti).

EXAMPLE 56

To 4.3 g of polyethylene powder are grafted 1.7 g of diallylamine (di-2-propenylamine). The irradiation intensity is 1.0 Mrad/hr, the absorbed dose is 60 Mrad. Polyethylene-gr.-polydiallylamine is processed with dry benzene and dried in a vacuum drier to constant weight. The yield of light yellow powder containing 0.35 percent of nitrogen is 4.0 g. The analysis of the I-R spectra of pressed films made out of this material shows that in addition to absorption bands characteristic of high-molecular crystalline non-branched polyethylene, there are also additional bands at 3380 $cm^{-1}$ which are due to the valency oscillations of associated N—H bonds, and also at 1612 and 1640 $cm^{-1}$, referring to deformational oscillations of the N—H bonds and to the terminal vinyl group (in combination with the band of medium intensity at 914 $cm^{-1}$). All of which proves the structure of the polymer polyethylene-gr.-polydiallylamine. The reaction between 2.3 g of the obtained product and 0.6 g of $TiCl_4$ is effected in conditions of Example 1. The yield of light yellow light brown powder containing 12.1 mg Ti/g, is 2.2 g.

The polymerization of ethylene is effected under the conditions of Example 1, except that the pressure of ethylene is 6 atm. The reactor is loaded with 0.0688 g of the obtained product and 150 ml of hexane and 0.44 g of $Al(C_2H_5)_2Cl$. The yield of high-molecular crystalline powder is 8.2 g (10 kg/g Ti). The molecular weight is 685,000.

EXAMPLE 57

Under the conditions of Example 1, to 71.0 g of polyethylene powder, grafted are 3.977 g of diallylamine. The irradiation intensity is 0.8 Mrad/hr, the absorbed dose 40 is Mrad. The yield of light-yellow powder, containing 0.45 percent of nitrogen, is 70.5 g. 10 g of the obtained polyethylene-gr.-polydiallylamine are processed with 6.1 percent solution of $VCl_4$ (15 ml) as in Example 1, to obtain 9.9 g of brown powder containing 1.92 percent of V. Ethylene is polymerized as in Example 1, except that the pressure of ethylene is 6 atm, and 150 ml of pure freshly distilled cyclohexane are used as the solvent. The reactor is loaded with 0.1585 g of the obtained product and 0.6795 g of $Al(C_2H_5)_2Cl$. The yield of crystalline polyethylene is 44 g (13.5 kg/g V). The molecular weight is 3,886,000.

EXAMPLE 58

The gaseous phase polymerization of ethylene is carried out in the absence of solvent. The reactor is loaded with 0.0946 g of the product prepared in Example 57, and 0.68 g of $Al(C_2H_5)_2Cl$ (solution in 5 ml of cyclohexane). The reaction is continued for three hours to give 14.5 g of polyethylene (8 kg/g V). The molecular weight is 1,621,000.

EXAMPLE 59

Reacted are 9 g of polyethylene-gr.-polydiallylamine, obtained in Example 57, and 1.95 g of $Ti(OC_4H_9)_4$, to prepare 8.5 g of white powder containing 0.7 mg Ti/g. The catalyst used in the polymerization process is 0.24 g of the obtained product and 0.64 g of $(iso-C_4H_9)_2AlCl$. Benzene is used as the solvent. The yield of polyethylene is 11 g (70 kg/g Ti). The molecular weight is 59,500.

EXAMPLE 60

Allylamine (3.044 g) is grafted to polyethylene (40.5 g) on an electron accelerator having the energy of 5 nev with a scattered beam of accelerated electrons, the energy of the beam being 1 kW. The total absorbed dose is 40 Mrad. The product is kept in benzene for three days and dried to constant weight. The yield of yellowish product containing 1.47 percent of nitrogen is 40.0 g. Additional absorption bands appear in infra-red spectrum of the obtained product, namely, a wide band with the maximum of absorption at 3380 $cm^{-1}$ (valency oscillations of $NH_2$ group), and 1070 $cm^{-1}$ (deformational oscillations N—H). This proves the structure of the obtained product: polyethylene-gr.-polyallylamine.

The reaction between 5 g of the polymer with 1.2 g of $VCl_4$ gives 4.9 g of dark brown powder containing 12.2 mg V/g. A reactor having the capacity of 1.3 liter is loaded with 250 ml of heptane, 0.156 g of the obtained product and 0.4 g of $Al(iso-C_4H_9)_2H$. The polymerization is carried out at a temperature of 70° C. and a pressure of 10 atmospheres. The yield of polyethylene is 154.5 (81.5 kg/g V.) The intrinsic viscosity is 13.3 (in tetraline at 135° C.); ash content is 0.02 percent.

EXAMPLE 61

The interaction between polyethylene-gr.-polyallylamine (5.0 g) obtained in Example 60, and 1.95 g of $Ti(OC_4H_9)_4$ in conditions of Example 1, gives 48 g of a white powder containing 0.3 mg Ti/g. Polymerization with this powder is carried out as in Example 60, except that 200 ml of benzene are used as the solvent. Loaded into the reactor are 0.24 g of the obtained product and 0.4 g of Al($C_2H_5$)$_2$Cl. The yield of polyethylene is 20.2 g (84 kg/g Ti).

EXAMPLE 62

The interaction between 4.9 g of polyethylene-gr.-polyallylamine and 0.1 g of ($C_5H_5$)$_2$TiCl$_2$ gives 3.7 g of slightly yellow powder containing 0.4 mg Ti/g. The reactor is loaded with 0.5 g of the obtained product and 0.45 g of Al(iso-$C_4H_9$)$_2$Cl and the polymerization is carried out in conditions described in Example 61. The yield of polyethylene is 10 g (50 kg/g Ti).

EXAMPLE 63

The interaction of 1.3 g of MoCl$_5$ with 5.0 g of polyethylene-gr.-polyallylamine under the conditions of Example 1 gives 4.7 g of brown product containing 11.0 mg of Mo/g. The polymerization of ethylene is carried out under the condition described in Example 61. Loaded into the reactor are 0.17 g of the obtained product and 0.74 g of Al($C_2H_5$)$_2$Cl. The yield of polyethylene is 3.7 g (2 kg/g Mo).

EXAMPLE 64

A glass ampoule provided with chambers for a polymer carrier and a grafted monomer is loaded with 37 g of low-pressure polyethylene (mol. wt. 928,000) and 3.7 g of pure freshly distilled acrylonitrile (stabilized for prevention of homopolymerization with 0.05 g of CuCl$_2$). The irradiation intensity is 1.1 Mrad/hr. the absorbed dose is 5.5 Mrad.

Nitrile fragments of polyethylene-gr.-polyacrylonitrile are reduced with LiAlH$_4$ as in Example 9. 5.4 g of the obtained reduced polyethylene-gr.-polyacrylonitrile are reacted in conditions of Example 1 with 1.1 g of TiCl$_4$. The yield of a brown-yellow powder containing 7.0 mg Ti/g, is 5.2 g. Polymerization with this product is carried out as described in Example 1, in benzene. The reactor is loaded with 0.144 g of the obtained product and 0.8 g of Al($C_2H_5$)$_2$Cl. The yield of polyethylene is 20.5 g (20.5 kg/g Ti).

EXAMPLE 65

3.1 g of allylmercaptan are grafted to 50.0 g of polyethylene powder as in Example 1. The irradiation intensity is, 0.3 Mrad/hr, the absorbed dose is 2.4 Mrad. The yield of a slightly yellow product —polyethylene-gr.-polyallylmercaptan, containing 0.16 percent of sulphur, is 50.2 g. The interaction of 8.0 g of the obtained polymer and 2.0 g of TiCl$_4$, with processing in conditions of Example 1, gives 7.8 g of yellow powder containing 0.7 mg Ti/g. A polymerization reactor is loaded with 0.3126 g of the obtained product and 0.4 g of Al($C_2H_5$)$_2$Cl and the polymerization is carried out as in Example 1. The yield of polyethylene is 4.5 g (20.5 kg/g Ti).

EXAMPLE 66

6.0 g of polyethylene-gr.-allylmercaptan are processed with 1.5 g of VCl$_4$ (solution in CCl$_4$) to prepare 5.9 g of gray powder containing 2.2 mg V/g. The polymerization is carried out as in Example 1. The reactor is loaded with 0.414 g of the prepared product and 0.4 g of Al($C_2H_5$)$_2$Cl. The polymerization is carried out as in Example 1. The reactor is loaded with 0.414 g of the obtained product and 0.4 g of Al($C_2H_5$)$_2$Cl. The polymerization is carried out in the course of three hours to obtain 28 g of polyethylene (31 kg/g V). The molecular weight is 2,085,000.

EXAMPLE 67

1.0 g of allylmercaptan is grafted to 4.3 g of copolymer of ethylene and propylene (content of methylene groups is 0.37/1000 carbon atoms, the intrinsic viscosity in tetraline at 135° C. is 2.03, the index of melt fluidity is 0.5 g/10 minutes, ash content is 0.018 percent). The ionizing radiation is 0.5 Mrad/hr, the absorbed dose is 7.0 Mrad. The processing of 4.4 g of the obtained poly-(ethylene-co-propylene)-gr.-polyallylmercaptan with 0.5 g of VCl$_4$ gives 4.2 g of dark-brown powder, containing 1.5 mg V/g.

A reactor is loaded with 0.3112 g of the obtained product and 0.6 g of Al(iso—$C_4H_9$)$_2$H (solvent —0.2 l of benzene), and the polymerization is continued in conditions of Example 1 for five hours to give 29 g of high-molecular polyethylene (62 kg/g V.).

EXAMPLE 68

Under the conditions of Example 1, 0.4 g of methylmercaptan is grafted to 2.7 g of polystyrene (absorbed dose of gamma radiation is 1.4 Mrad). Reacted are 2.9 g of the obtained polystryene-gr.-polymethylmethycrylate with VCl$_4$ to prepare 2.2 g of brown powder- complex compound of VCl$_4$ with polystyrene-gr.-polymetacrylate- the component A of the catalyst of polymerization containing 9 mg V/g. Under the conditions of Example 1, the reactor is loaded with 0.1248 g of the obtained product and 0.48 g of Al($C_2H_5$)$_2$Cl. The yield of high-molecular crystalline polyethylene is 46 g (41 kg/g V).

EXAMPLE 69

Interacted are 3.7 g of polyethylene-gr.-polymethylvinylketone obtained in Example 9, and 0.7 g of VCl$_4$ in a medium of CCl$_4$, to prepare 3.6 g of complex compounds of VCl$_4$ with polyethylene-gr.-polymethylvinylketone, containing 7.2 mg of V/g. The reactor is loaded with 0.1523 g of the obtained product and 0.4 g of Al($C_2H_5$)$_2$Cl. The polymerization is continued for two hours under conditions of Example 1 to prepare 57.5 g of high-molecular crystalline polyethylene (57.5 kg/g V). The intrinsic viscosity in tetraline is 16.0 (at 135° C.).

EXAMPLE 70

A reactor is loaded with 0.1428 g of the product obtained in Example 69 and 0.7 g of Al(iso-$C_4H_9$)$_2$Cl. The gaseous mixture delivered into the reactor for copolymerization contains 58.6 percent by volume of ethylene and 41.4 percent by volume of propylene, the total pressure of the monomers being 6.66 atm. 200 ml of n-heptane are used as solvent. The copolymerization is continued for four hours to give 26 g of high-elasticity copolymer of ethylene with propylene, that is completely soluble in n-heptane at a temperature of polymerization (70° C.).

EXAMPLE 71

The interaction of TiCl$_4$ with polyethylene-gr.-polyacrylonitrile obtained in Example 64 takes place under the conditions of Example 1. 1.4 g of polyethylene-gr.-polyacrylonitrile and 0.5 g of TiCl$_4$ give 1.6 g of a light yellow product containing 18 mg Ti/g. The polymerization is carried out as in Example 1. Loaded into a reactor are 0.2015 g of the obtained product and 0.8 g of Al(C$_2$H$_5$)$_2$Cl. The yield of high-molecular crystalline polyethylene is 45 g (12.5 kg/g Ti).

EXAMPLE 72

7.8 g of acrylonitrile are grafted to 180 g of polypropylene powder. Ionizing radiation is 40 rad/sec (0.144 Mrad/hour). The absorbed dose is 0.86 Mrad. The interaction of VCl$_4$ (0.5 g) with polypropylene-gr.-polyacrylonitrile (7.0 g) is as in Example 1.

The yield is 6.8 g of a light brown powder containing 0.9 mg V/g. The polymerization of propylene is carried out as in Example 1. The pressure is 5.0 atm. Loaded are 0.5 g of the obtained product and 0.96 g of Al(C$_2$H$_5$)$_2$Cl. The yield is 3.7 g of polypropylene (8 kg/g V).

EXAMPLE 73

Grafted, as in Example 1, is 0.9 g of pure freshly distilled 2-vinylpyridine to 7.4 g of polyethylene powder. The product is processed with 1.3 g of VCl$_4$, as in Example 1, to prepare 8.0 g of light brown powder containing 4.3 mg V/g of the product —VCl$_4$ bonded chemically with polyethylene-gr.-poly(2-vinylpyridine). A reactor is loaded with 0.2 g of the obtained product and 0.64 g of Al(C$_2$H$_5$)$_2$Cl, and the polymerization is carried out as in Example 1. The yield of polyethylene is 8.7 g (10 kg/g V.).

EXAMPLE 74

An ampoule for radiation-chemical grafting is loaded with 12 g of polypropylene, to which is grafted is 1.1 g of 4-vinylpyridine (irradiation intensity is 0.5 Mrad/hour), absorbed dose is 4.7 Mrad). After keeping the obtained product in boiling benzene for ten hours and drying to constant weight, the yield of polypropylene-gr.-poly(4-vinylpyridine) is 12.7g.

Interacted, as in Example 1, are 3.4 g of the obtained polymer and 0.7 g of CoCl$_2$, to obtain 3.5 g of gray powder containing 12 mg Co/g. A reactor, under the conditions of Example 1, is loaded with 0.25 g of the obtained product and 0.64 g of Al(iso-C$_4$H$_9$)$_2$Cl. The yield of polyethylene is 7.5 g (2.5 kg/g Co).

EXAMPLE 75

The interaction under conditions of Example 1 of 4.3 g of polypropylene-gr.-poly(4-vinylpyridine) with 0.8 g of VCl$_4$ gives 4.5 g of brown powder containing 14 mg of V/g. The reactor is loaded with 0.2 g of the obtained product and 0.4 g of Al(C$_2$H$_5$)$_2$Cl. Ethylene is polymerized as in Example 1 to prepare 6.9 g of polyethylene (24 kg/g V).

EXAMPLE 76

Diallyl sulphide (0.6 g) is grafted to polyethylene (4.2 g) and the obtained polyethylene-gr.-polydiallyl sulphide is processed with VCl$_4$ as described in Example 1 to obtain 4.0 g of light brown product containing 1.2 g of V/g. 0.4274 g of the obtained complex compound is loaded into the reactor as in Example 1, 0.4 g of Al(C$_2$H$_5$)$_2$ Cl is added. The yield of high-molecular polyethylene is 14.5 kg (28 kg/g V).

EXAMPLE 77

Under the conditions of Example 1 (except that the ionizing radiation intensity is 0.75 Mrad/hour, and the total absorbed dose is 15 Mrad) 0.6 g of diallylsulphone is grafted to 7.0 g of polyethylene. The resulting polyethylene-gr.-polydiallylsulphone is processed with VCl$_4$ (0.6 g) to prepare 6.9 g of pale brown product containing 3.1 mg V/g. The polymerization is carried out as in Example 1: loaded are 0.5 g of the obtained product and 0.4 g of Al(C$_2$H$_5$)$_2$Cl. The yield of polyethylene is 17 g (11 kg/g V).

EXAMPLE 78

A three-neck flask (evacuated and then blown with argon) is loaded with 15.0 g of polypropylene-gr.-polyacrylonitrile obtained in Example 72, and 100 ml of freshly distilled n-heptan. The components are intensively stirred and the reaction mixture is heated to 60° C. Added gradually from a dividing funnel are 2.4 g of Al(C$_2$H$_5$)$_3$ (a solution in 50 ml of n-heptane). The reaction is carried out for three hours at the same temperature. The suspension is then transferred in an inert atmosphere onto a filter, washed with four portions of n-heptane, and dried in vacuum. The yield is 16.0 g of bright yellow powder containing 0.019 g/g aluminium. The powder is component B of the catalyst of polymerization of olefins.

The absorption band at 2240 cm$^{-1}$, which is characteristic of the valency oscillations of the group —C≡N, is absent in the I-R spectrum of the obtained product, but a new band with the maximum of absorption at 1630 cm$^{-1}$, characteristic of the valency oscillations of the group —C=N—, appears instead. The structure of the obtained product can be described schematically as

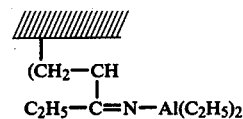

Together with the data of chemical analysis this testifies to a 100 percent transformation of the nitrile groups.

EXAMPLE 79

A glass ampoule is loaded with 10.2 g of polyethylene powder (low pressure) and it is irradiated for thirty minutes with a high-frequency discharge, after which 2.1 g of gaseous acrylonitrile are added to the thus obtained polyethylene. After grafting, the product is washed with benzene and dried in a vacuum drier to constant weight. The yield is 11.7 g of polyethylene-gr.-polyacrylonitrile containing 0.135 g of polyacrylonitrile per gram of the product. Under the conditions of Example 1 5.4 g of polyethylene-gr.-polyacrylonitrile and 1.35 g of Al(iso-C$_4$H$_9$)$_2$H are reacted to give 6.4 g of bright yellow powder containing 0.0374 g Al/g. The obtained product is component B of the catalyst of polymerization of olefins.

EXAMPLE 80

A glass ampoule for radiation polymerization is loaded with 70 g of low-pressure polyethylene (sp.surface 1.6 sq.m/g) and 3.0 g of freshly distilled methylvinylketone stabilized with 0.1 g of CuCl$_2$. The grafting is carried out with ionizing radiation of 0.15 Mrad/hr, the exposure being 10 hours, and the absorbed dose 1.5 Mrad. After washing the obtained product and drying it to constant weight, the yield of polyethylene-gr.-polymethylvinylketone, containing 0.034 g of polymethylvinylketone in one gram of the product, is 72 g. In conditions of Example 1, reacted are Al(C$_2$H$_5$)$_3$ with polyethylene-gr.-polymethylvinylketone. The reactants are taken in the following quantities: polyethylene-gr.- polymethylvinylketone — 6.8 and Al(C$_2$H$_5$)$_3$ — 0.4 g. The yield of a white powder, containing 0.055 g/g, is 7.1 g. This is component B of the catalyst for polymerization of olefins. The absorption band characteristic of valency oscillations of carbonyl groups (1728 cm$^{-1}$) is absent in the I-R spectrum of the obtained compound; the product has the following structure:

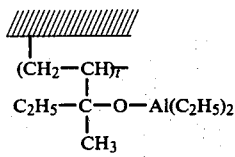

EXAMPLE 81

A reactor is evacuated, then blown with ethylene, and 1.330 g of the product of interaction of polypropylene-gr.-polyacrylonitrile with Al(C$_2$H$_5$)$_3$, obtained in Example 78, and containing 0.019 g Al/g of the product, and 200 ml of pure, freshly distilled n-heptane are loaded into it. The capacity of the reactor is 1.3 liter. Now ethylene is delivered into the reactor at a temperature of 70° C. and a pressure of 10.0 atm. The polymerization begins after adding 1.5 mg of VCl$_4$ (freshly prepared solution in n-heptane) and is continued for two hours (the temperature of polymerization of ethylene pressure being maintained constant throughout the entire polymerization process). The polymer is washed with ethyl alcohol, water, and dried in a vacuum drier. The yield of high-molecular crystalline polyethylene is 12.5 g (8.3 kg/g VCl$_4$, or 31.0 kg/g V, and 0.55 kg/g Al).

EXAMPLE 82

Under the conditions of Example 81, except that 250 ml of pure, freshly distilled benzene are used as the solvent, 0.4084 g of the product of interaction between polyethylene-gr.-polyacrylonitrile and Al(iso-C$_4$H$_9$)$_2$H, prepared in Example 72 and containing 0.0374 gAl/g, and also 2.5 g of TiCl$_4$ (in n-heptane) are polymerized for three hours. The resulting polymer is processed as in Example 81 and the yield of high-molecular crystalline polyethylene is 11.0 g (4.4 kg/g TiCl$_4$, or 18 kg/g Ti, and 0.73 kg/g Al).

EXAMPLE 83

Under the conditions of Example 82, the reactor is loaded with 0.485 g of the product of interaction of polyethylene-gr.-polymethylvinylketone with Al(C$_2$H$_5$)$_3$, obtained in Example 80, and 1.2 mg of VOCl$_3$ (solution in n-heptane). The polymerization is continued for two hours to give 17.3 g of high-molecular crystalline polyethylene (14.5 kg/g VOCl$_3$, or 50 kg/g V, and 0.64 kg/g Al).

EXAMPLE 84

A three-neck flask provided with a stirrer, a reflux condenser, and a dividing funnel is loaded with 12.0 g of polyethylene-gr.-polyallyl alcohol, obtained in Example 24, 70 ml of pure and freshly distilled n-heptane. Now 1.1 g of toluene solution of tetrabenzyl-titanium Ti(CH$_2$C$_6$H$_5$)$_4$ (concentration 0.1 mole/liter) is added dropwise from a dividing funnel in the course of two hours at a temperature of 60° C. The reaction is continued for another two hours at the same temperature. The product is separated on a filter, washed with n-heptane in an inert atmosphere (three portions of 50 ml), and dried in vacuum to constant weight. The yield of a yellowish powder, containing 0.35 mg Ti/g, is 11.8 g.

Under the conditions of Example 1, except that benzene is used as solvent, the reactor is loaded with 0.9237 g of the obtained product. The yield of high-molecular crystalline polyethylene is 6.9 g (17 kg/g Ti). The ash content is 0.01 percent.

EXAMPLE 85

Under the conditions of Example 84, the reactor is loaded with 0.623 g of the product obtained in this Example. The yield of high-molecular polyethylene is 5.1 g (20 kg/g Ti).

EXAMPLE 86

Under the conditions of Example 83 (except that toluene is used as the solvent, and the temperature of the reaction is 30° C.) are reacted 4.0 g of polyethylene-gr.-allyl alcohol with 0.45 g of tetrabenzyl-vanadium V(CH$_2$C$_6$H$_5$)$_4$ to give 3.8 g of light brown powder containing 0.42 g of V/g. The reactor is loaded in conditions of Example 84 with 0.8344 g of the obtained product to prepare 14.0 g of high-molecular crystalline polyethylene (38 kg/g V). The ash content is 0.01 percent.

EXAMPLE 87

Under the conditions of Example 84, reacted are 8.6 g of polyethylene-gr.-polydiallylamine, obtained in Example 57, and 0.89 g of tetrabenzyl-titanium. The yield of pale yellow powder is 8.4 g. The content of Ti is 0.28 mg/g of the product. The reactor is loaded with 0.4412 g of the obtained product, the polymerization is carried out as in Example 84, but the length of the polymerization process is six hours. The yield of polyethylene is 5.3 g (40 kg/g Ti). The ash content, 0.01 percent.

What is claimed is:

1. A catalyst of polymerization, copolymerization and oligomerization of olefins and diolefins, which is one of the following components: component A having the general formula MX$_n$ wherein M is a metal belonging to IVA-VIA groups of the Periodic System or cobalt, X is a halogen, hydrogen, cyclopentadienyl, alkoxy-, aryloxy- or amide group, and n is an integer denoting the valency of M; component B which is an organometallic compound having the general formula M'R$_p$Z$_{k-p}$ wherein M' is a metal belonging to I − III groups of the Periodic System, R is a hydrocarbon radical, z is a halogen, hydrogen, alkoxy-, aryloxy- or amide group, and k is an integer denoting the valency of M', $1 \leq p \leq k$; and component C which is a product having the general formula MR$_m$X$_{n-m'}$, wherein n is an integer, $2 \leq m \leq n$, said component being chemically bonded to the surface of one of the fragments of the carbon-chain polymer carrier having grafted thereto substituents having the formula

wherein:
R' = H, CH$_3$, C$_2$H$_5$, CH$_2$ = CH, or C$_6$H$_5$;
R'' = H, or CH$_3$;
R''' = H, or CH$_3$;
Y = OH, NHR', SR', COCH$_3$, CH$_2$OH,

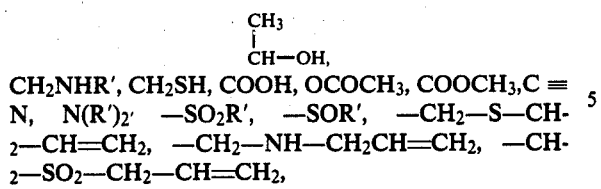
CH₂NHR', CH₂SH, COOH, OCOCH₃, COOCH₃, C≡N, N(R')₂, —SO₂R', —SOR', —CH₂—S—CH₂—CH=CH₂, —CH₂—NH—CH₂CH=CH₂, —CH₂—SO₂—CH₂—CH=CH₂,

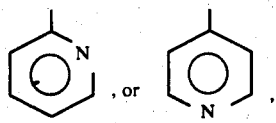

wherein R' is as defined above,
t is a mean degree of polymerization, equal to 4–5000, and, after bonding, component A is in mixture with compound M'R$_p$Z$_{k-p}$ and component B is in mixture with compound MX$_n$.

2. A catalyst as claimed in claim 1, wherein the molar ratio between M', in M'R$_p$Z$_{k-p}$, and M, in component A, is 5 to 500, preferably 10 to 100.

3. A catalyst in claim 1, wherein the molar ratio between M', in component B, and M, in MX$_n$, is 20 to 200, preferably 50 to 100.

4. A catalyst as claimed in claim 1, wherein used as component A is a compound having said formula MX$_n$, chemically bonded through the fragment

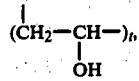

in which t = 50 to 1500, with the surface of a polymer carrier, in admixture with one of said organometallic compounds having the formula M'R$_p$Z$_{k-p}$.

5. A catalyst as claimed in claim 1, wherein used as component A is a compound having said formula MX$_n$, chemically bonded through the fragment

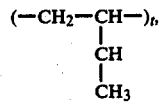

in which t = 100 to 2000, with the surface of a polymer carrier, in admixture with one of said organometallic compounds having the formula M'R$_p$Z$_{k-p}$.

6. A catalyst as claimed in claim 1, wherein used as component A is a compound having said formula MX$_n$, chemically bonded through the fragment

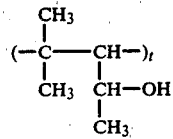

in which t = 30 to 300, with the surface of a polymer carrier, in admixture with one of said organometallic compounds having the formula M'R$_p$Z$_{k-p}$.

7. A catalyst as claimed in claim 1, wherein used as component A is a compound having said formula MX$_n$, chemically bonded through the fragment

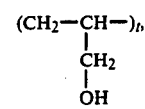

in which t = 4 to 9, with the surface of a polymer carrier, in admixture with one of said organometallic compounds having the formula M'R$_p$Z$_{k-p}$.

8. A catalyst as claimed in claim 1, wherein used as component A is a compound having said formula MX$_n$, chemically bonded through the fragment

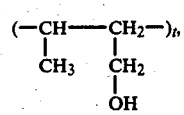

in which t = 4 to 9, with the surface of a polymer carrier, in admixture with one of said organometallic compounds having the formula M'R$_p$Z$_{k-p}$.

9. A catalyst as claimed in claim 1, wherein used as component A is a compound having said formula MX$_n$, chemically bonded through the fragment

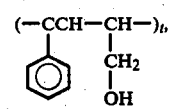

in which t = 4 to 9, with the surface of a polymer carrier, in admixture with one of said organometallic compounds having the formula M'R$_p$Z$_{k-p}$.

10. A catalyst as claimed in claim 1, wherein used as component A is a compound having said formula MX$_n$, chemically bonded through the fragment

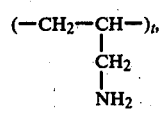

in which t = 500 to 2000, with the surface of a polymer carrier, in admixture with one of said organometallic compounds having the formula M'R$_p$Z$_{k-p}$.

11. A catalyst as claimed in claim 1, wherein used as component A is a compound having said formula MX$_n$, chemically bonded through the fragment

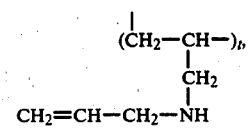

in which t = 4 to 9, with the surface of a polymer carrier, in admixture with one of said organometallic compounds having the formula M'R$_p$Z$_{k-p}$.

12. A catalyst as claimed in claim 1, wherein used as component A is a compound having said formula MX$_n$, chemically bonded through the fragment (CH₂—CH—)ₜ,
|
CH₂
|
NH₂ in which t = 4 to 9, with the surface of a polymer carrier, in admixture with one of said organometallic compounds having the formula M′R$_p$Z$_{k-p}$.

13. A catalyst as claimed in claim 1, wherein used as component A is a compound having said formula MX$_n$, chemically bonded through the fragment (CH₂—CH—)ₜ,
|
CH₂
|
SH in which t = 4 to 9, with the surface of a polymer carrier, in admixture with one of said organometallic compounds having the formula M′R$_p$Z$_{k-p}$.

14. A catalyst as claimed in claim 1, wherein used as component A is a compound having said formula MX$_n$, chemically bonded through the fragment

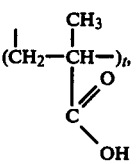

in which t = 100 to 2000, with the surface of a polymer carrier, in admixture with one of said organometallic compounds having the formula M′R$_p$Z$_{k-p}$.

15. A catalyst as claimed in claim 1, wherein used as component A is a compound having said formula MX$_n$, chemically bonded through the fragment (CH₂—CH—)ₜ,
|
CH₂
|
C≡N in which t = 500 to 2000, with the surface of a polymer carrier, in admixture with one of said organometallic compounds having the formula M′R$_p$Z$_{k-p}$.

16. A catalyst as claimed in claim 1, wherein used as component A is a compound having said formula MX$_n$, chemically bonded through the fragment

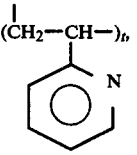

in which t = 500 to 5000, with the surface of a polymer carrier, in admixture with one of said organometallic compounds having the formula M′R$_p$Z$_{k-p}$.

17. A catalyst as claimed in claim 1, wherein used as component A is a compound having said formula MX$_n$, chemically bonded through the fragment

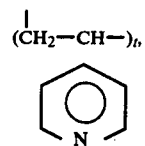

in which t = 500 to 5000, with the surface of a polymer carrier, in admixture with one of said organometallic compounds having the formula M′R$_p$Z$_{k-p}$.

18. A catalyst as claimed in claim 1, wherein used as component A is a compound having said formula MX$_n$, chemically bonded through the fragment

CH₃
|
(CH₂—C—)ₜ,
|
C=O
|
O—CH₃ in which t = 400 to 4000, with the surface of a polymer carrier, in admixture with one of said organometallic compounds having the formula M′R$_p$Z$_{k-p}$.

19. A catalyst as claimed in claim 1, wherein used as component A is a compound having said formula MX$_n$, chemically bonded through the fragment

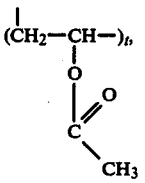

in which t = 50 to 1500, with the surface of a polymer carrier, in admixture with one of said organometallic compounds having the formula M′R$_p$Z$_{k-p}$.

20. A catalyst as claimed in claim 1, wherein used as component A is a compound having said formula MX$_n$, chemically bonded through the fragment (CH₂—CH—)ₜ,
|
C=O
|
CH₃ in which t = 500 to 2000 with the surface of a polymer carrier, in admixture with one of said organometallic compounds having the formula M′R$_p$Z$_{k-p}$.

21. A catalyst as claimed in claim 1, wherein used as component A is a compound having said formula MX$_n$, chemically bonded through the fragment (CH₂—CH—)ₜ,
|
CH₂
|
S
|
CH₂=CH—CH₂ in which t = 4 to 9, with the surface of a polymer carrier, in admixture with one of said organometallic compounds having the formula M′R$_p$Z$_{k-p}$.

22. A catalyst as claimed in claim 1, wherein used as component A is a compound having said formula $MX_n$, chemically bonded through the fragment

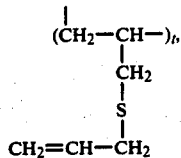

in which t = 4 to 9, with the surface of a polymer carrier, in admixture with one of said organometallic compounds having the formula $M'R_pZ_{k-p}$.

23. A catalyst as claimed in claim 1, wherein used as component B is an organometallic compound having said formula $M'R_pZ_{k-p}$, chemically bonded through the fragment

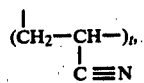

in which t = 500 to 2000, with the surface of a polymer carrier, in admixture with a compound having the formula $MX_n$.

24. A catalyst as claimed in claim 1, wherein used as component B is an organometallic compound having said formula $M'R_pZ_{k-p}$, chemically bonded through the fragment

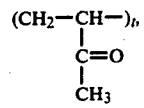

in which t = 100 to 2000, with the surface of a polymer carrier, in admixture with a compound having the formula $MX_n$.

25. A catalyst as claimed in claim 1, wherein component C is the product of interaction of $MX_n$ and $M'R_pZ_{k-p}$, having the formula $MR_mX_{n-m}$, in which M, X, n, M', m, R, Z, p and k have values according to claim 1, and chemically bonded through the fragment

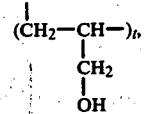

in which t = 4 to 9, with the surface of a polymer carrier.

26. A catalyst as claimed in claim 1, wherein component C is the product of interaction of $MX_n$ and $M'R_pZ_{k-p}$, having the formula $MR_mX_{n-m}$ and chemically bonded through the fragment

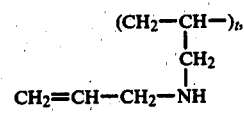

in which t = 4 to 9, with the surface of a polymer carrier.